US009849169B2

(12) United States Patent
Nagy et al.

(10) Patent No.: US 9,849,169 B2
(45) Date of Patent: Dec. 26, 2017

(54) MDR *E. COLI* SPECIFIC ANTIBODY

(71) Applicant: ARSANIS BIOSCIENCES GMBH, Vienna (AT)

(72) Inventors: Eszter Nagy, Vienna (AT); Gábor Nagy, Sopron (HU); Valéria Szijártó, Vienna (AT); Zoltán Magyarics, Vienna (AT); Irina Mirkina, Vienna (AT); Luis Guachalla, Vienna (AT); Adriana Badarau, Vienna (AT); Gerhild Zauner, Vienna (AT); Jolanta Lukasiewicz, Wroclaw (PL)

(73) Assignee: ARSANIS Biosciences GmbH, Vienna (AT)

( * ) Notice: Subject to any disclaimer, the term of this patent is extended or adjusted under 35 U.S.C. 154(b) by 0 days.

(21) Appl. No.: 14/651,156

(22) PCT Filed: Jan. 17, 2014

(86) PCT No.: PCT/EP2014/050895
§ 371 (c)(1),
(2) Date: Jun. 10, 2015

(87) PCT Pub. No.: WO2014/111516
PCT Pub. Date: Jul. 24, 2014

(65) Prior Publication Data
US 2015/0322138 A1    Nov. 12, 2015

(30) Foreign Application Priority Data

Jan. 17, 2013   (EP) .................................... 13151627

(51) Int. Cl.
| | | |
|---|---|---|
| *G01N 33/569* | (2006.01) | |
| *A61K 39/108* | (2006.01) | |
| *C07K 16/12* | (2006.01) | |
| *A61K 39/00* | (2006.01) | |

(52) U.S. Cl.
CPC ...... *A61K 39/0258* (2013.01); *C07K 16/1232* (2013.01); *G01N 33/56916* (2013.01); *A61K 2039/505* (2013.01); *A61K 2039/55505* (2013.01); *A61K 2039/55511* (2013.01); *A61K 2039/55561* (2013.01); *C07K 2317/33* (2013.01); *C07K 2317/73* (2013.01); *C07K 2317/92* (2013.01); *G01N 2333/245* (2013.01); *G01N 2469/10* (2013.01)

(58) Field of Classification Search
None
See application file for complete search history.

(56) References Cited

U.S. PATENT DOCUMENTS 6,331,415 B1   12/2001   Cabilly et al.
6,858,211 B1   2/2005    Szu et al.

FOREIGN PATENT DOCUMENTS

WO        93/03765 A1    3/1993

OTHER PUBLICATIONS

Vajdos et al. (J Mol Biol. Jul. 5, 2002;320(2):415-28.*
Brown et al. (J Immunol. May 1996;156(9):3285-91.*
International Search Report dated Mar. 14, 2014, in connection with corresponding International Application No. PCT/EP2014/050895.
Written Opinion of the International Searching Authority dated Mar. 14, 2014, in connection with corresponding International Application No. PCT/EP2014/050895.
Extended European Search Report dated Mar. 28, 2013, in connection with corresponding EP Application No. 13151627.0.
O. Clermont, et al., "Rapid detection of the O25b-ST131 clone of *Escherichia coli* encompassing the CTX-M-15-producing strains", Journal of Antimicrobial Chemotherapy, 2009, vol. 64, pp. 274-277.
S. Jadhav, et al., "Virulence Characteristics and Genetic Affinities of Multiple Drug Resistant Uropathogenic *Escherichia coli* from a Semi Urban Locality in India", PLOS One, 2011, vol. 6, Issue 3 (7 pages).
A. Mora, et al., "Emergence of clonal groups O1:HNM-D-ST59, O15:H1-D-ST393, 020:H34/HNM-D-ST354, O25b:H4-B2-ST131 and ONT:H21, 42-B1-ST101 among CTX-M-14-producing *Escherichia coli* clinical isolates in Galicia, northwest Spain", International Journal of Antimicrobial Agents, 2011, vol. 37, No. 1, pp. 16-21.
B. A. Rogers, et al., "*Escherichia coli* O25b-ST131: a pandemic, multiresistant, community-associated strain", Journal of Antimicrobial Chemotherapy, 2011, vol. 66, No. 1, pp. 1-14.
V. Szijarto, et al., "The rapidly emerging ESBL-producing *Escherichia coli* O25-ST131 clone carries LPS core synthesis genes of the K-12 type", FEMS Microbiology Letters, 2012, vol. 332, pp. 131-136.
R. Stenutz, et al., "The structures of *Escherichia coli* O-polysaccharide antigens", FEMS Microbiol. Rev., May 2006, vol. 30, No. 3, pp. 382-403.
B. R. Brodeur, et al., "Mouse-Human Myeloma Partners for the Production of Heterohybridomas", Monoclonal Antibody Production Techniques and Applications, Marcel Dekker, Inc., 1987, pp. 51-63.
J. Wibbenmeyer, et al., "Cloning, expression, and characterization of the Fab fragment of the anti-lysozyme antibody HyHEL-5", Biochimica et Biophysica Acta, 1999, vol. 1430, No. 2, pp. 191-202.
N. Woodford, et al., "Multiresistant Gram-negative bacteria: the role of high-risk clones in the dissemination of antibiotic resistance", FEMS Microbiol Rev, 2011, vol. 35, No. 5, pp. 736-755.
K. A. Duda, et al., "The lipopolysaccharide of the mastitis isolate *Escherichia coli* strain 1303 comprises a novel O-antigen and the rare K-12 core type", Microbiology, 2011, vol. 157, Pt. 6, pp. 1750-1760.
L. Kenne, et al., "Structural Studies of the *Escherichia coli* O-Antigen 25", Carbohydrate Research, 1983, vol. 122, No. 2, pp. 249-256.
G. Kohler, et al., "Continuous cultures of fused cells secreting antibody of predefined specificity", Nature, Aug. 7, 1975, vol. 256, pp. 495-497.
D. Kozbor, et al., "A Human Hybrid Myeloma for Production of Human Monoclonal Antibodies", The Journal of Immunology, Dec. 1984, vol. 133, No. 6, pp. 3001-3005.

(Continued)

*Primary Examiner* — Brian Gangle
(74) *Attorney, Agent, or Firm* — Maier & Maier, PLLC

(57) ABSTRACT

The subject relates to an isolated antibody that specifically binds to O25b antigen of multi drug resistant (MDR) *E. coli* strains, its medical and diagnostic use, method of producing the antibody, including an isolated nucleotide sequence, plasmids and host cells as used in the production of the antibody; and further an isolated epitope recognized the specific antibody.

5 Claims, 7 Drawing Sheets

(56) References Cited

OTHER PUBLICATIONS

Figure 2:
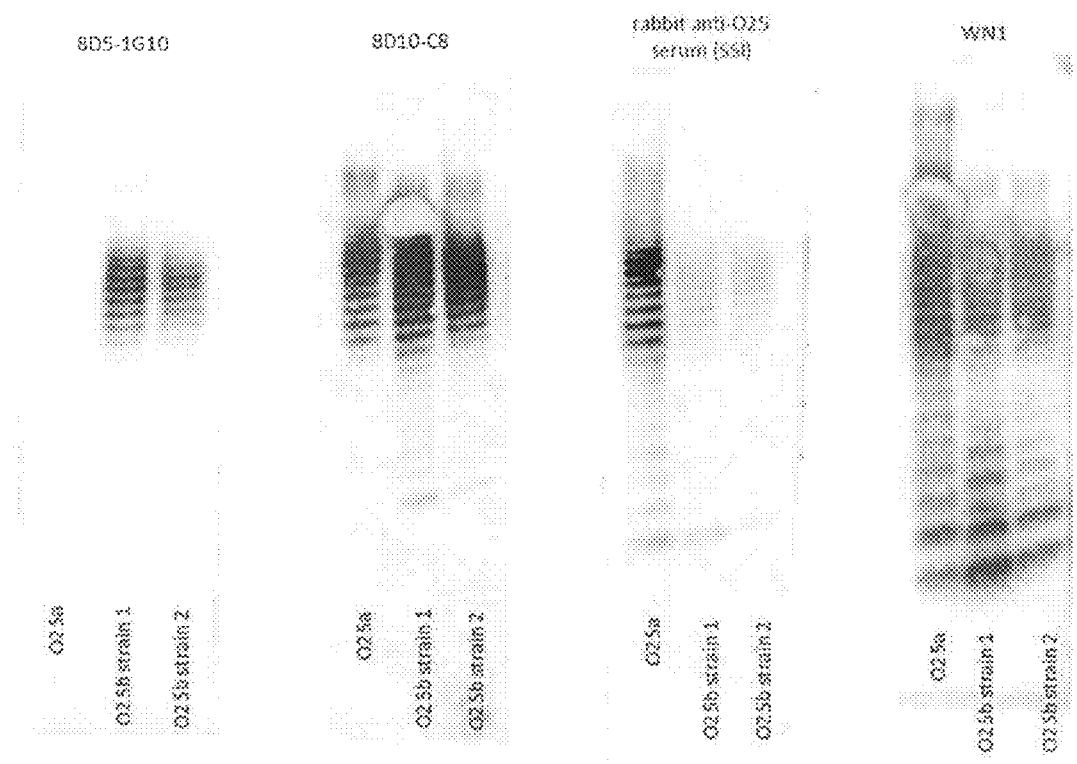

Myung-Hoon Lee, et al., "Expression and functional reconstitution of a recombinant antibody (Fab') specific for human apolipoprotein B-100", Journal of Biotechnology, 2003, vol. 101, pp. 189-198.

S. Muller-Loennies, et al., "Structural Analysis of Oligosaccharides from Lipopolysaccharide (LPS) of *Escherichia coli* K12 Strain W3100 Reveals a Link between Inner and Outer Core LPS Biosynthesis", The Journal of Biological Chemistry, Sep. 5, 2003, vol. 278, No. 36, pp. 34090-34101.

G. Peirano, et al., "Molecular characteristics of extended-spectrum β-lactamase-producing *Escherichia coli* from the Chicago area: high prevalence of ST131 producing CTX-M-15 in community hospitals", International Journal of Antimicrobial Agents, 2010, vol. 36, pp. 19-23.

Extended European Search Report dated Mar. 14, 2017, including the European Search Report and the European Search Opinion, in connection with corresponding EP Application No. 16201732.1 (10 pgs).

European Office Action dated Mar. 7, 2017, in connection with corresponding EP Application No. 14703782.2 (7 pgs.).

Valéria Szijártó, et al., "Diagnostic Potential of Monoclonal Antibodies Specific to the Unique O-Antigen of Multidrug-Resistant Epidemic *Escherichia coli* Clone ST131-O25b:H4" in Clinical and Vaccine Immunology, Jul. 2014, vol. 21, No. 7, pp. 930-939 (10 pgs.).

Valéria Szijártó, et al., "Bactericidal Monoclonal Antibodies Specific to the Lipopolysaccharide O Antigen from Multidrug-Resistant *Escherichia coli* Clone ST131-O25b:H4 Elicit Protection in Mice" in Antimicrobial Agents and Chemotherapy, Jun. 2015, vol. 59, No. 6, pp. 3109-3116 (8 pgs.).

Gábor Nagy, et al., "Lipopolysaccharide: a tool and target in enterobacterial vaccine development", in Biological Chemistry, Jan. 2008, vol. 389, No. 5, 8 pgs. (XP055349068).

S. J. Cryz, Jr., et al., "Synthesis and Characterization of *Escherichia coli* O18 O-Polysaccharide Conjugate Vaccines", in Infection and Immunity, Feb. 1990, vol. 58, No. 2, pp. 373-377 (5 pgs.).

Simone Cagnacci, et al., "European Emergence of Ciprofloxacin-Resistant *Escherichia coli* Clonal Groups O25:H4-ST 131 and O15:K52:H1 Causing Community-Acquired Uncomplicated Cystitis", in the Journal of Clinical Microbiology, Aug. 2008, vol. 46, No. 8, pp. 2605-2612 (8 pgs.).

Olivier Clermont, et al., "The CTX-M-15-producing *Escherichia coli* diffusing clone belongs to a highly virulent B2 phylogenetic subgroup", in the Journal of Antimicrobial Chemotherapy, 2008, vol. 61, No. 5, pp. 1024-1028 (5 pgs).

\* cited by examiner

Fig. 1
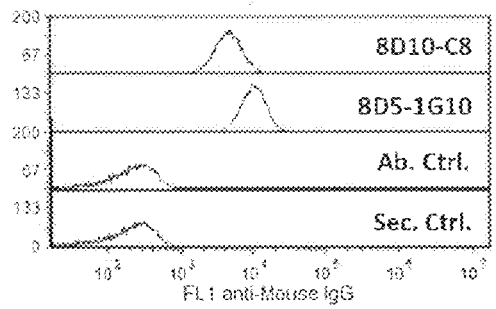
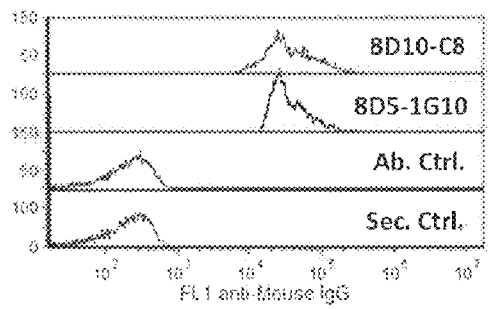
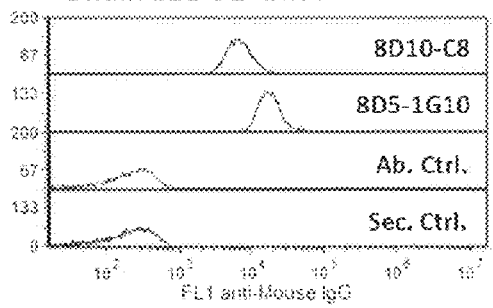
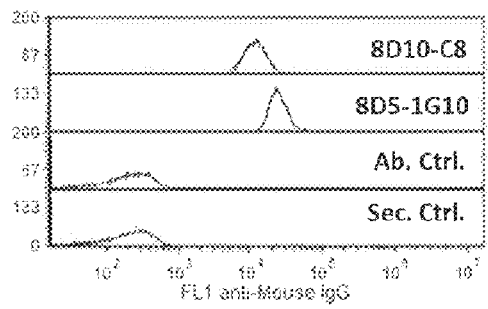
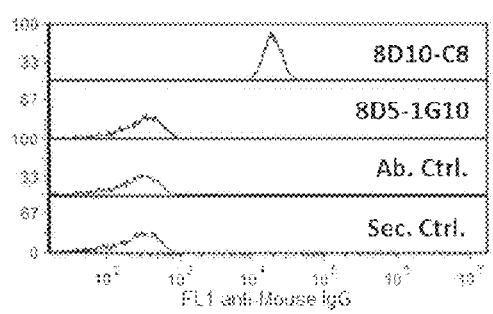
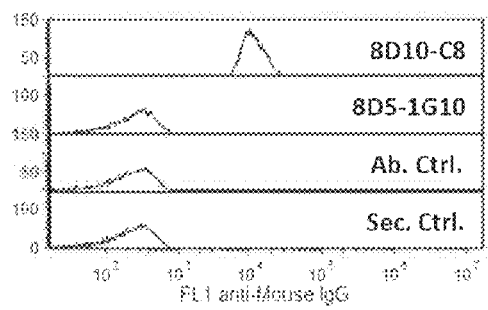
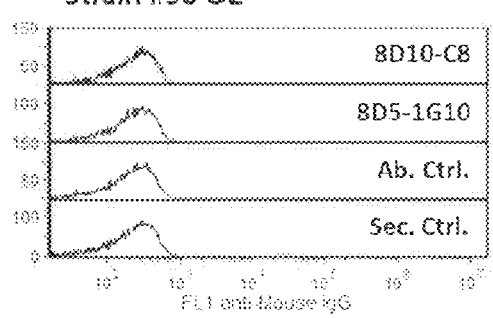

Fig. 3
(a): O25b
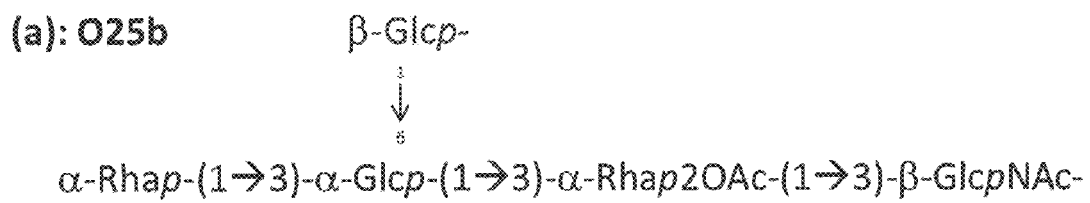
(b): O25a
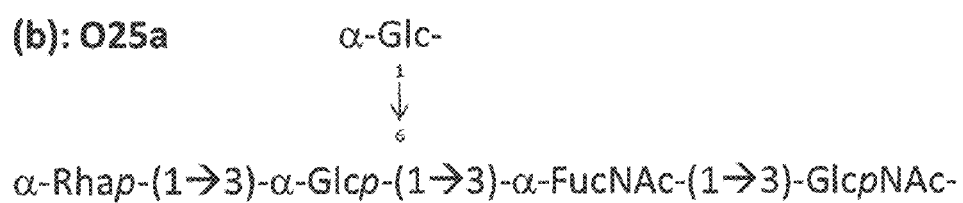

O25b       O25       O2

MDR E. COLI SPECIFIC ANTIBODY

FIELD OF THE INVENTION

The invention refers to an antibody specifically binding to the LPS O25b antigen of multi drug resistant (MDR) *E. coli* strains.

BACKGROUND OF THE INVENTION

Lipopolysaccharide (LPS) is the most abundant antigen on the surface of enterobacterial pathogens. Typically, LPS has three structural parts: i) Lipid A (also known as endotoxin), ii) core oligosaccharide, and iii) O-antigen. The latter is made up of repeating subunits of 3-6 sugars (depending on the serotype). Lipid A and core OS are relatively well conserved in one single enterobacterial species, however, their accessibility to antibodies are limited. On the other hand, O-antigens are highly accessible, but very diverse with respect to their structure (in *E. coli* there are ~180 different O-types).

Antibodies against O-antigens are able to bind to the surface of *E. coli*, hence they are used both for diagnostics (e.g. O-typing for epidemiology studies) as well as are proposed as therapeutic measures. Nevertheless, given the huge structural variability, a broad spectrum protection with O-antigen specific antibodies is cumbersome.

Extraintestinal infections caused by *E. coli* are common causing significant morbidity and mortality. Multi-drug resistant (MDR) strains of *E. coli* that have emerged recently cause a significant proportion of *E. coli* infections.

Treatment options against these MDR strains are getting very limited as they have evolved resistance to most classes of clinically relevant antibiotics. Therefore, an alternative treatment option, e.g. passive immunization with monoclonal antibodies (mAbs) holds a great promise for the future.

In the past years a well-defined clonal lineage of MDR *E. coli*. the ST131-O25b:H4 has emerged causing approximately 10% of all extraintestinal *E. coli* infections and about half of the MDR *E. coli* infections (Peirano et al. Int J Antimicrob Agents 2010 April; 35(4):316-21; Rogers et al. J Antimicrob Chemother 2011 January; 66(1):1-14; Woodford et al. FEMS Microbiol Rev 2011 September; 35(5): 736-55.). Strains belonging to this lineage show limited heterogeneity thus could be considered very similar with respect to antigenic repertoire. The vast majority of the strains belonging to this cluster express the O25b antigen and hence a specific gene (within the LPS synthesis locus) encoding for enzymes synthesizing this antigen is used for the identification of this clone (Clermont et al. J Antimicrob Chemother 2008 May; 61(5):1024-8.). Alternatively, agglutination with the O25 typing sera can be used, in spite that the O antigen of this lineage differ from the classical O25 antigen (hence it had been termed O25b) as suggested by genetic differences. However, the O25 typing sera can not distinguish between the non-MDR O25 and the MDR O25b clones.

Rogers et al. (J Antimicrob Chemother 2011 January; 66(1):1-14) describe the detection of the *E. coli* O25b-ST131 strain by three major characteristics, i.e. its serogroup (O25b), its phylogenetic group (B2) and its ST (ST131). Each of these characteristics is disclosed to aid detection. A variety of molecular techniques is described, i.e. MLST, PCR-based rapid detection methods, repetitive sequence PCR and PFGE. Polyclonal antisera (raised against an O25a strain) including a variety of immunoglobulins have been used to determine the O25 antigen, not differentiating subtypes.

Jadhav et al. (PLOS ONE 2011; 6(3): e18063) describe the virulence characteristics and genetic affinities of strains which were positive for the O25b subgroup that is linked to the B2-O25b-ST131-CTX-M-15 virulent/multiresistant type. Human clinical isolates were analyzed and classified into serotypes and virulence marker profiles were obtained. O25 positive strains were identified by serotyping using polyclonal antisera against O-antigens—O1 to O173. The O25 positive strains were further subjected to genotyping by an allele-specific PCR targeting the rfbO25b subgroup gene locus.

Mora et al. (Int. J. Antimicrobial Agents 2011; 37(1): 16-21) describe the emergence of some clonal groups among CTX-M-14 producing *E. coli* clinical isolates, among them O25b: H4-B2-ST131. O typing was done with specific O antisera (polyclonal).

Clermont et al. (J Antimicrob Chemother 2008 May; 61(5):1024-8) discloses an allele-specific pabB PCR assay specific for O25b ST131 *E. coli*.

Szijarto et al, (FEMS Microbiol Lett 2012; 332:131-6) describe molecular typing of *E. coli* strain isolates based on the core structure of the LPS molecule. The core type of the isolates was determined by PCR using primers targeting genes in the core operon and specific to R1-4 and K-12 core types, respectively.

SUMMARY OF THE INVENTION

It is the objective of the present invention to provide for an antibody directed against MDR strains of *E. coli* with improved specificity to be used for the prevention or therapy of *E. coli* infections caused by LPS O25b carrying strains. It is further the objective to provide means and methods that are capable of diagnosing MDR *E. coli* bacteria in a rapid and reliable manner.

The object is solved by the subject of the present invention.

According to the invention there is provided an isolated antibody that specifically binds to O25b antigen of multi drug resistant (MDR) *E. coli* strains.

Specifically, the antibody is a monoclonal antibody.

Specifically, the antibody is specific to bind O25b antigen only, or cross-specific to bind an epitope shared by the O25a and O25b antigens.

According to a specific aspect, the antibody is cross-specific to bind the O25b and O25 or O25a antigens, e.g. with equal, more than equal, similar or different affinities.

Specifically, the antibody of the invention preferentially binds to the O25b antigen relative to the O25a antigen of *E. coli*, or at least with equal affinity towards both antigens.

According to a specific embodiment, the antibody has at least two-fold greater affinity for binding the O25b antigen as compared to the O25a antigen, specifically with at least two-fold difference, or at least three-fold, at least four-fold, at least 5-fold, or even at least 10-fold difference in binding either the O25b or the O25a antigen, e.g. difference in affinity and/or avidity.

According to a specific aspect the specific binding to O25b is characterized by the greater affinity for binding the O25b antigen as compared to binding the O25b antigen by a polyclonal serum raised against O25 or O25a *E. coli* strains as determined by immunoassay, preferably immunoblotting, ELISA or other immunological methods. The higher binding affinity is specifically with at least two-fold difference, or at least three-fold, at least four-fold, at least 5-fold, or even at least 10-fold difference.

Specifically, the O25b antigen as targeted by the antibody of the invention is prevalent in one or more, and more specifically present in the vast majority of ST131 strains.

Specifically, the epitope recognized by the antibody is present on the surface of encapsulated and non-encapsulated ST131-O25b:H4 strains, e.g. mutant strains.

According to a further specific aspect, the antibody has a binding site of a full-length monoclonal antibody or an antibody fragment thereof comprising at least one antibody domain incorporating a binding site, which antibody is preferably an antibody selected from the group consisting of murine, lama, rabbit, goat, cow, chimeric, humanized or human antibodies, heavy-chain antibodies, Fab, Fd, scFv and single-domain antibodies like VH, VHH or VL, preferably a human IgG antibody or a murine IgG antibody.

According to a further specific aspect, the antibody has an affinity to bind the O25b antigen with a Kd of less than $10^{-7}$ M, preferably less than $10^{-8}$ M, specifically in a monomeric state.

According to a further specific aspect, the antibody exhibits in vitro bactericidal potency in a serum sample comprising live wild-type MDR *E. coli* strains.

According to a further specific aspect, the antibody stimulates uptake of live wild-type MDR *E. coli* strains by phagocytic cells in vitro.

According to a further specific aspect, the antibody binds the same epitope as the antibody designated as 8D5-1G10 or 8D10-C8.

According to a further specific aspect, the antibody comprises the same binding site as the antibody designated as 8D5-1G10 or 8D10-C8.

According to a specific aspect, the invention provides for an isolated monoclonal antibody that specifically binds to O25b antigen of multi drug resistant (MDR) *E. coli* strains which comprises the antigen-binding site of antibody 8D5-1G10, or which is derived from the antibody 8D5-1G10, or a functionally active variant of the antibody 8D5-1G10, preferably wherein the antibody 8D5-1G10 is characterized by
 a) the variable region of the antibody light chain produced by the host cell deposited under DSM 26763; and/or
 b) the variable region of the antibody heavy chain produced by the host cell deposited under DSM 26762;
 c) or a functionally active variant of (a) and/or (b) is employed.

According to a specific embodiment, the antibody is the 8D5-1G10 antibody, or a functionally active variant thereof.

Further antibodies of the invention are exemplified herein, which are designated 6D1-1B2 and 8A1-1G8. These are clones with CDR sequences similar to the 8D5-1G10, herein also understood as functionally active CDR variants.

Specifically, the antibody designated as 8D5-1G10 is composed of an antibody light chain comprising the variable region encoded by the coding sequence of the plasmid comprised in the *E. coli* host cell deposited under DSM 26763, and an antibody heavy chain comprising the variable region encoded by the coding sequence of the plasmid comprised in the *E. coli* host cell deposited under DSM 26762.

According to a further specific aspect, the antibody is derived from the 8D5-1G10 antibody, wherein
 the variable region of the antibody light chain is encoded by a plasmid comprised in the *E. coli* host cell deposited under DSM 26763, or a functionally active variant thereof; and/or
 the variable region of the antibody heavy chain is encoded by a plasmid comprised in the *E. coli* host cell deposited under DSM 26762, or a functionally active variant thereof.

According to a further specific aspect, the antibody is derived from an antibody, wherein
 the variable region of the antibody light chain is produced by a host cell deposited under DSM 26763, or a functionally active variant thereof; and/or
 the variable region of the antibody heavy chain is produced by a host cell deposited under DSM 26762, or a functionally active variant thereof.

According to another specific aspect, the invention provides for an isolated monoclonal antibody which is cross-specific to bind an epitope shared by the O25a and O25b antigens, and which comprises the antigen-binding site of antibody 8D10-C8, or which is derived from the antibody 8D10-C8, or a functionally active variant of the antibody 8D10-C8, preferably wherein the antibody 8D10-C8 is characterized by
 a) the variable region of the antibody light chain produced by the host cell deposited under DSM 28171; and/or
 b) the variable region of the antibody heavy chain produced by the host cell deposited under DSM 28172;
 c) or a functionally active variant of (a) and/or (b) is employed.

According to a specific embodiment, the antibody is the 8D10-C8 antibody, or a functionally active variant thereof.

Specifically, the antibody designated as 8D10-C8 is composed of an antibody light chain comprising the variable region encoded by the coding sequence of the plasmid comprised in the *E. coli* host cell deposited under DSM 28171, and an antibody heavy chain comprising the variable region encoded by the coding sequence of the plasmid comprised in the *E. coli* host cell deposited under DSM 28172.

According to a further specific aspect, the antibody is derived from the 8D10-C8 antibody, wherein
 the variable region of the antibody light chain is encoded by a plasmid comprised in the *E. coli* host cell deposited under DSM 28171, or a functionally active variant thereof; and/or
 the variable region of the antibody heavy chain is encoded by a plasmid comprised in the *E. coli* host cell deposited under DSM 28172, or a functionally active variant thereof.

According to a further specific aspect, the antibody is derived from an antibody, wherein
 the variable region of the antibody light chain is produced by a host cell deposited under DSM 28171, or a functionally active variant thereof; and/or
 the variable region of the antibody heavy chain is produced by a host cell deposited under DSM 28172, or a functionally active variant thereof.

Specifically, the functionally active variant is a CDR variant, e.g. which comprises a CDR, more specifically a CDR loop sequence, with an amino acid sequence having at least 60% sequence identity, preferably at least 70%, 80% or 90% sequence identity.

Specifically, the antibody is derived from such antibodies, employing the respective CDR sequences, or CDR mutants, including functionally active CDR variants, e.g. with 1, 2 or 3 point mutations within one CDR loop.

Specifically, the functionally active variant differs from the parent antibody in at least one point mutation in the amino acid sequence, preferably in the CDR, wherein the number of point mutations in each of the CDR amino acid sequences is either 0, 1, 2 or 3.

According to a further specific aspect, the invention provides for a plasmid comprising a nucleotide sequence A
encoding the variable region of the antibody light chain designated 8D5-1G10-LC comprised in a host cell deposited under DSM 26763; and/or
encoding the variable region of the antibody heavy chain designated 8D5-1G10-HC comprised in a host cell deposited under DSM 26762;

or B
encoding the variable region of the antibody light chain designated 8D10-C8-LC comprised in a host cell deposited under DSM 28171; and/or
encoding the variable region of the antibody heavy chain designated 8D10-C8-HC comprised in a host cell deposited under DSM 28172.

According to a further specific aspect, the invention provides for an expression cassette comprising a coding sequence to express a light chain and/or heavy chain of an antibody of the invention, which expression cassette or coding sequence is derived from a plasmid selected from the group consisting of a plasmid of the invention.

According to a further specific aspect, the invention provides for a method of producing an antibody of the invention, wherein a host cell is transformed with a plasmid of the invention or the expression cassette of the invention.

According to a further specific aspect, the invention provides for a host cell comprising a plasmid of the invention or the expression cassette of the invention.

Specifically, the host cell is deposited under
A
DSM 26763 and/or DSM 26762;
or B
DSM 28171 and/or DSM 28172.

A specific embodiment refers to a method of producing an antibody of the invention, wherein a host cell of the invention is cultivated or maintained under conditions to produce said antibody.

According to a further specific aspect, the invention provides for a method of identifying a candidate antibody comprising:
(a) providing a sample containing an antibody or antibody-producing cell; and
(b) assessing for binding of an antibody in or produced by the sample with an epitope recognized by the antibody designated as 8D5-1G10 or 8D10-C8, wherein a positive reaction between the antibody and the epitope identifies the antibody as candidate antibody.

According to a further specific aspect, the invention provides for a method of identifying a candidate antibody comprising:
(a) providing a sample containing an antibody or antibody-producing cell; and
(b) assessing for binding of an antibody in or produced by the sample with O25b antigen of an ST131-O25b:H4 strain and O25 antigen of a non-MDR *E. coli* strain, or the O25a antigen, wherein a specific positive reaction between the antibody and the O25b antigen relative to the O25 antigen or O25a antigen identifies the antibody as candidate antibody.

Specifically, the candidate antibody is a candidate protective antibody, such as for therapeutic use, or a candidate diagnostic antibody.

Yet, according to a further specific aspect, the invention provides for a method of producing an antibody of the invention, comprising (a) providing a candidate antibody identified according to the invention; and
(b) producing a monoclonal antibody, or a humanized or human form of the candidate antibody, or a derivative thereof with the same epitope binding specificity as the candidate antibody.

According to another specific aspect, the invention provides for a method of producing an antibody of the invention, comprising
(a) immunizing a non-human animal with an epitope recognized by the antibody designated as 8D5-1G10 or 8D10-C8;
(b) forming immortalized cell lines from the isolated B-cells;
(c) screening the cell lines obtained in b) to identify a cell line producing a monoclonal antibody that binds to the epitope; and
(d) producing the monoclonal antibody, or a humanized or human form of the antibody, or a derivative thereof with the same epitope binding specificity as the monoclonal antibody.

According to another specific aspect, the invention provides for a method of producing an antibody of the invention, comprising
(a) immunizing a non-human animal with O25b antigen of a ST131-O25b:H4 strain and isolating B-cells producing antibodies;
(b) forming immortalized cell lines from the isolated B-cells;
(c) screening the cell lines to identify a cell line producing a monoclonal antibody that preferentially binds to the O25b antigen relative to the O25 antigen or O25a antigen of *E. coli*; and
(d) producing the monoclonal antibody, or a humanized or human form of the antibody, or a derivative thereof with the same epitope binding specificity as the monoclonal antibody.

According to a further aspect, the invention provides for the medical use of an antibody of the invention. Specifically, the antibody is provided for use in treating a subject at risk of or suffering from a MDR *E. coli* infection comprising administering to the subject an effective amount of the antibody to limit the infection in the subject or to ameliorate a disease condition resulting from said infection, preferably for treatment or prophylaxis of pyelonephritis, secondary bacteremia, sepsis, peritonitis, meningitis, and ventilator-associated pneumonia.

Specifically, the antibody is provided for bactericidal killing of MDR *E. coli*, preferably a ST131-O25b:H4 strain irrespective of capsular polysaccharide expressed by the strain.

According to a specific aspect, there is further provided a method of treatment wherein a subject at risk of or suffering from a MDR *E. coli* infection is treated, which method comprises administering to the subject an effective amount of the antibody to limit the infection in the subject or to ameliorate a disease condition resulting from said infection, preferably a method for treatment or prophylaxis of pyelonephritis, secondary bacteremia, sepsis, peritonitis, meningitis, and ventilator-associated pneumonia.

Specifically, the method of treatment is provided for bactericidal killing of MDR *E. coli*, preferably a ST131-O25b:H4 strain irrespective of capsular polysaccharide expressed by the strain.

According to a specific aspect, immunotherapy using the antibody of the invention may effectively protect against live bacterial challenge, e.g. as determined in various animal models.

The antibody may specifically neutralize lethal endotoxaemia. Such functional activity may be determined in an appropriate in vivo model (challenge with purified LPS).

The antibody is specifically effective against MDR E. coli by complement-mediated killing, e.g. as determined by an in vitro serum bactericidal assay (SBA), e.g. with at least 20% killing of bacteria above the control samples (no antibody or irrelevant control mAb added).

The antibody is specifically effective against MDR E. coli by antibody mediated phagocytosis, e.g. as determined by an in vitro opsonophagocytotic killing assay (OPK), e.g. with at least 20% uptake of input bacteria or 20% lower end cfu count above the control samples (no antibody or irrelevant control mAb added).

The antibody is specifically effective against MDR E. coli by neutralizing endotoxin functions, e.g. as determined by an in vitro LAL assay, or toll-like receptor 4 (TLR4) reporter assay e.g. with at least 20% reduction in endotoxin activitiesin comparison to control samples (no antibody or irrelevant control mAb added).

According to a specific embodiment, the antibody is administered in a parenteral or mucosal formulation.

According to a further aspect, the invention provides for a pharmaceutical preparation of an antibody of the invention, preferably comprising a parenteral or mucosal formulation, optionally containing a pharmaceutically acceptable carrier or excipient.

According to a further aspect, the invention provides for an antibody of the invention, for diagnostic use to detect or determine E. coli infection in a subject caused by MDR strains expressing the LPS O25b antigen, such as with upper and lower urinary tract infections, including cystitis or urethritis, ascending or hematogenous pyelonephritis, especially in diabetic patients, as well as with bacteremia, sepsis, peritonitis, or intestinal colonization.

Specifically, the antibody is provided for use according to the invention, wherein a systemic infection with MDR E. coli in a subject is determined ex vivo by contacting a sample of body fluid of said subject with the antibody, wherein a specific immune reaction of the antibody determines the infection.

Specifically, a sample of body fluid is tested for the specific immune reaction, which sample is selected from the group consisting of urine, blood, blood isolates or blood culture, aspirate, sputum, lavage fluid of intubated subjects and stool.

Specifically, the diagnostic use according to the invention refers to determining the serotype of E. coli in vitro from a pure E. coli culture recovered from a clinical specimen.

According to a further aspect, the invention provides for a diagnostic preparation of an antibody of the invention, optionally containing the antibody with a label and/or a further diagnostic reagent with a label, such as a reagent specifically recognizing the antibody or an immune complex of the antibody with the respective target antigen, and/or a solid phase to immobilize at least one of the antibody and the diagnostic reagent. The diagnostic preparation may be provided as a composition or as a kit of parts, e.g. comprising components, such as components comprising a) the diagnostic antibody preparation, and/or
b) the further diagnostic reagent,
and/or a solid phase to immobilize at least one of the antibody and the diagnostic reagent, either as a separate component or as a carrier of any of components a) and/or b) above.

Preferred diagnostic assays of the invention comprise the antibody of the invention immobilized on a solid phase, e.g. latex beads, gold particles, etc., e.g. to test agglutination by the antibody of bacteria expressing O25b antigen or free (or isolated) O25b antigen obtained from a sample to be tested.

Some diagnostic assays may involve two different antibodies with different specificity and/or affinity to bind O25b and/or O25a, so to possibly differentiate between the O25b and O25a antigens.

According to a specific aspect, the invention provides for companion diagnostics to determine the infection of a subject with MDR E. coli by the diagnostics of the invention or the diagnostic method of the invention, to provide for the basis of treatment with a therapeutic against such infection, e.g. employing immunotherapy, such as treating with an antibody of the invention.

According to a specific aspect, the invention provides for a sensitive bedside diagnostics to diagnose infection of a subject with MDR E. coli by determining free LPS, e.g. from clinical specimen where the amount of live bacteria is limited. The sensitivity of such assay is specifically less than 100 ng preferably less than 10 ng of LPS.

According to a further aspect, the invention provides for an isolated epitope recognized by the antibody designated 8D5-1G10 or 8D10-C8. Such epitope may consist of a single epitope or a mixture of epitopes comprising epitope variants, each recognized by the specific antibody designated 8D5-1G10 or 8D10-C8. Specifically, the epitope of the 8D10-C8 antibody is a shared one and prevalent on both the O25b and O25a antigens, thus, the antibody is considered as being cross-specific, yet preferentially binding the O25b antigen at least with equal as binding the O25a antigen.

According to a further aspect, the invention provides for an immunogen comprising:
  (a) an epitope of the invention;
  (b) optionally further epitopes not natively associated with said epitope of (a); and
  (c) a carrier.

Specifically, the carrier is a pharmaceutically acceptable carrier, preferably comprising buffer and/or adjuvant substances.

The immunogen of the invention is preferably provided in a vaccine formulation, preferably for parenteral use.

Specifically the immunogen of the invention is provided for medical use, specifically for use in treating a subject by administering an effective amount of said immunogen to protect the subject from an MDR E. coli infection, or to prevent a disease condition resulting from said infection.

Specifically the immunogen of the invention is provided for eliciting a protective immune response.

According to a specific aspect, there is further provided a method of treatment wherein a subject at risk of an MDR E. coli infection is treated, which method comprises administering to the subject an effective amount of the immunogen to prevent infection in the subject, in particular to protect against pathogenic MDR E. coli.

According to a further aspect, the invention provides for an isolated nucleic acid encoding an antibody of the invention, or encoding an epitope of the invention.

FIGURES

FIG. 1: Surface staining of different ST131:O25b strains expressing O25b, O25a, or O2 antigens by O25b-specific (with or without cross-reactivity to O25a antigen) mAbs.

FIG. 2: reactivity of different mAbs and O25 rabbit serum to purified O25a and O25b LPS molecules in an immunoblot assay.

FIG. 3: (a): Structure of the repeating unit of *E. coli* O25b antigen. (b): structure of the repeating unit of *E. coli* O25a (also referred to O25, sometimes referred to as O25(a)) for comparison (Kenne et al, 1985).

Figure 4:
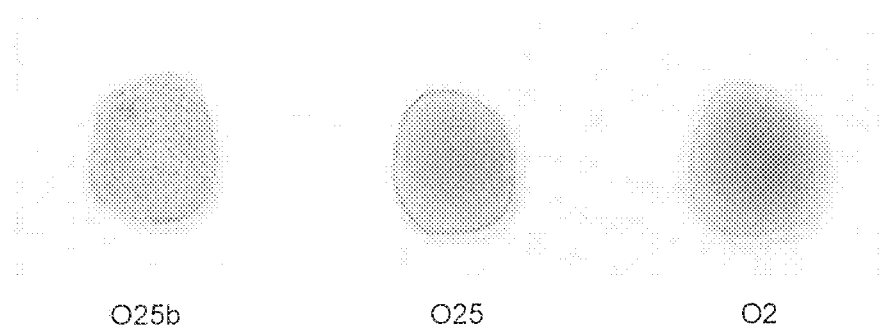

FIG. 4: Detection of O25b antigen expressing *E. coli* strains with agglutination assay using mAb 8D5-1G10 coupled to latex beads.

Figure 5:
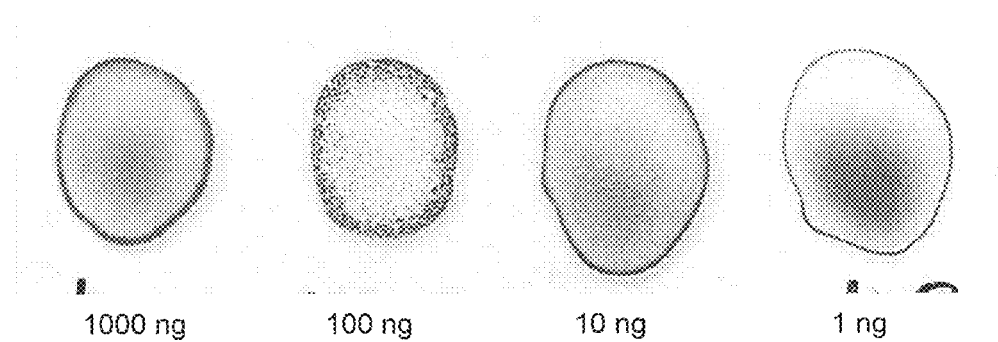

FIG. 5: Detection of soluble O25b antigen with agglutination assay using mAb 8D5-1G10 coupled to latex beads.

Figure 6:
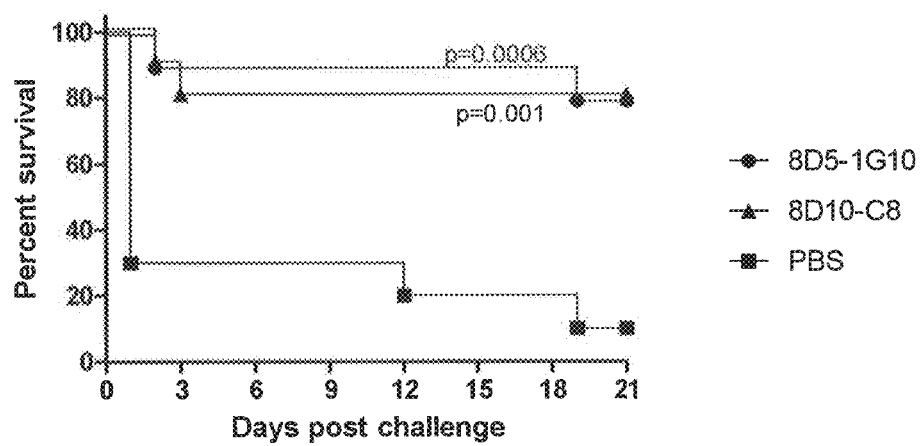

FIG. 6: Protection provided by passive immunization of mice with O25b-specific murine mAbs against a subsequent intravenous lethal challenge by an ST131:O25b clinical isolate.

Figure 7:
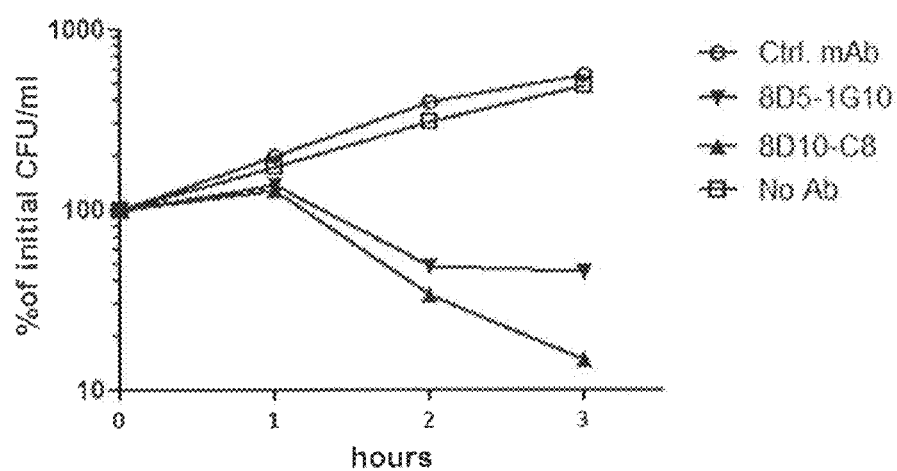

FIG. 7: Complement dependent bacterial killing mediated by the O25b specific mAbs.

DETAILED DESCRIPTION

The term "antibody" as used herein shall refer to polypeptides or proteins that consist of or comprise antibody domains, which are understood as constant and/or variable domains of the heavy and/or light chains of immunoglobulins, with or without a linker sequence. Polypeptides are understood as antibody domains, if comprising a beta-barrel structure consisting of at least two beta-strands of an antibody domain structure connected by a loop sequence. Antibody domains may be of native structure or modified by mutagenesis or derivatization, e.g. to modify the antigen binding properties or any other property, such as stability or functional properties, such as binding to the Fc receptors FcRn and/or Fcgamma receptor.

The antibody as used herein has a specific binding site to bind one or more antigens or one or more epitopes of such antigens, specifically comprising a CDR binding site of a single variable antibody domain, such as VH, VL or VHH, or a binding site of pairs of variable antibody domains, such as a VL/VH pair, an antibody comprising a VL/VH domain pair and constant antibody domains, such as Fab, F(ab'), (Fab)$_2$, scFv, Fv, or a full length antibody.

The term "antibody" as used herein shall particularly refer to antibody formats comprising or consisting of single variable antibody domain, such as VH, VL or VHH, or combinations of variable and/or constant antibody domains with or without a linking sequence or hinge region, including pairs of variable antibody domains, such as a VL/VH pair, an antibody comprising or consisting of a VL/VH domain pair and constant antibody domains, such as heavy-chain antibodies, Fab, F(ab'), (Fab)$_2$, scFv, Fd, Fv, or a full-length antibody, e.g. of an IgG type (e.g., an IgG1, IgG2, IgG3, or IgG4 subtype), IgA1, IgA2, IgD, IgE, or IgM antibody. The term "full length antibody" can be used to refer to any antibody molecule comprising at least most of the Fc domain and other domains commonly found in a naturally occurring antibody monomer. This phrase is used herein to emphasize that a particular antibody molecule is not an antibody fragment.

The term "antibody" shall specifically include antibodies in the isolated form, e.g. that are substantially free of other antibodies directed against different target antigens or comprising a different structural arrangement of antibody domains. Still, an isolated antibody may be comprised in a combination preparation, containing a combination of the isolated antibody, e.g. with at least one other antibody, such as monoclonal antibodies or antibody fragments having different specificities.

The term "antibody" shall apply to antibodies of animal origin, including human species, such as mammalian, including human, murine, rabbit, goat, lama, cow and horse, or avian, such as hen.

The term "antibody" further applies to chimeric antibodies with sequences of origin of different species, such as sequences of murine and human origin.

The term "chimeric" as used with respect to an antibody refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. For example, the variable region can be derived from presently known sources using readily available B-cells or hybridomas from non-human host organisms in combination with constant regions derived from, for example, human cell preparations.

The term "antibody" further applies to humanized antibodies.

The term "humanized" as used with respect to an antibody refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified, e.g. by one or more amino acid substitutions, preferably modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "antibody" further applies to human antibodies.

The term "human" as used with respect to an antibody, is understood to include antibodies having variable and constant regions derived from human germline immunoglobulin sequences. The human antibody of the invention may include amino acid residues not encoded by human germline immunoglobulin sequences (e.g., mutations introduced by random or site-specific mutagenesis in vitro or by somatic mutation in vivo), for example in the CDRs. Human antibodies include antibodies isolated from human immunoglobulin libraries or from animals transgenic for one or more human immunoglobulin.

The term specifically applies to antibodies of any class or subclass. Depending on the amino acid sequence of the constant domain of their heavy chains, antibodies can be assigned to the major classes of antibodies IgA, IgD, IgE, IgG, and IgM, and several of these may be further divided into subclasses (isotypes), e.g., IgG1, IgG2, IgG3, IgG4, IgA, and IgA2.

The term further applies to monoclonal or polyclonal antibodies, specifically a recombinant antibody, which term includes all antibodies and antibody structures that are prepared, expressed, created or isolated by recombinant means, such as antibodies originating from animals, e.g. mammalians including human, that comprises genes or sequences from different origin, e.g. chimeric, humanized antibodies, or hybridoma derived antibodies. Further examples refer to antibodies isolated from a host cell transformed to express the antibody, or antibodies isolated from a recombinant, combinatorial library of antibodies or antibody domains, or antibodies prepared, expressed, created or isolated by any other means that involve splicing of antibody gene sequences to other DNA sequences.

It is understood that the term "antibody" also refers to derivatives of an antibody, in particular functionally active derivatives. An antibody derivative is understood as any combination of one or more antibody domains or antibodies and/or a fusion protein, in which any domain of the antibody may be fused at any position of one or more other proteins, such as other antibodies, e.g. a binding structure comprising CDR loops, a receptor polypeptide, but also ligands, scaffold proteins, enzymes, toxins and the like. A derivative of the antibody may be obtained by association or binding to other substances by various chemical techniques such as covalent coupling, electrostatic interaction, di-sulphide bonding etc. The other substances bound to the antibody may be lipids, carbohydrates, nucleic acids, organic and inorganic molecules or any combination thereof (e.g. PEG, prodrugs or drugs). In a specific embodiment, the antibody is a derivative comprising an additional tag allowing specific interaction with a biologically acceptable compound. There is not a specific limitation with respect to the tag usable in the present invention, as far as it has no or tolerable negative impact on the binding of the antibody to its target. Examples of suitable tags include His-tag, Myc-tag, FLAG-tag, Strep-tag, Calmodulin-tag, GST-tag, MBP-tag, and S-tag. In another specific embodiment, the antibody is a derivative comprising a label. The term "label" as used herein refers to a detectable compound or composition which is conjugated directly or indirectly to the antibody so as to generate a "labeled" antibody. The label may be detectable by itself, e.g. radioisotope labels or fluorescent labels, or, in the case of an enzymatic label, may catalyze chemical alteration of a substrate compound or composition which is detectable.

The preferred derivatives as described herein are functionally active with regard to the antigen binding, preferably which have a potency to combat MDR *E. coli* and its endotoxin, e.g. as determined in an SBA, OPK or LAL assay, or to protect against bacterial challenge or to neutralize lethal endotoxemia.

Antibodies derived from a parent antibody or antibody sequence are herein particularly understood as mutants or variants obtained by e.g. in silico or recombinant engineering or else by chemical derivatization or synthesis.

Specifically, an antibody derived from an antibody of the invention may comprise at least one or more of the CDR regions or CDR variants thereof being functionally active in differentially binding to the O25b antigen, e.g. specifically or selectively binding the O25b antigen.

It is understood that the term "antibody" also refers to variants of an antibody.

The term "variant" shall particularly refer to antibodies, such as mutant antibodies or fragments of antibodies, e.g. obtained by mutagenesis methods, in particular to delete, exchange, introduce inserts into a specific antibody amino acid sequence or region or chemically derivatize an amino acid sequence, e.g. in the constant domains to engineer the antibody stability, effector function or half-life, or in the variable domains to improve antigen-binding properties, e.g. by affinity maturation techniques. Any of the known mutagenesis methods may be employed, including point mutations at desired positions, e.g. obtained by randomisation techniques. In some cases positions are chosen randomly, e.g. with either any of the possible amino acids or a selection of preferred amino acids to randomise the antibody sequences. The term "mutagenesis" refers to any art recognized technique for altering a polynucleotide or polypeptide sequence. Preferred types of mutagenesis include error prone PCR mutagenesis, saturation mutagenesis, or other site directed mutagenesis.

The term "variant" shall specifically encompass functionally active variants.

The term "functionally active variant" of an antibody as used herein, means a sequence resulting from modification of this sequence (a parent antibody or a parent sequence), e.g. by insertion, deletion or substitution of one or more amino acids, such as by recombination techniques or chemical derivatization of one or more amino acid residues in the amino acid sequence, or nucleotides within the nucleotide sequence, or at either or both of the distal ends of the sequence, and which modification does not affect (in particular impair) the activity of this sequence. In the case of a binding site having specificity to a selected target antigen, the functionally active variant of an antibody would still have the predetermined binding specificity, though this could be changed, e.g. to change the fine specificity to a specific epitope, the affinity, the avidity, the Kon or Koff rate, etc. Specifically, the functionally active variants of an antibody of the invention have the potency to bind O25b antigen and the specificity or selectivity to preferentially bind to the O25b antigen relative to other antigens of *E. coli*, e.g. binding to O25b and not binding to the O25a antigen of *E. coli*, or not significantly binding the O25a antigen, or cross-specifically binding both, O25b and O25a antigens, but not binding to other antigens of *E. coli*.

Functionally active variants may be obtained, e.g. by changing the sequence of a parent antibody, e.g. an antibody comprising the same binding site as the antibody designated 6D1-1B2, 8A1-1G8, 8D5-1G10, or 8D10-C8, but with modifications within an antibody region besides the binding site, or derived from a parent antibody, which is any of the 6D1-1B2, 8A1-1G8, 8D5-1G10, or 8D10-C8 antibodies, by a modification within the binding site but that does not impair the antigen binding, and preferably would have a biological activity similar to the parent antibody, including the ability to specifically or selectively bind O25b antigen, e.g. binding to O25b and not binding to the O25a antigen of *E. coli*, or not significantly binding the O25a antigen, or cross-specifically binding both, O25b and O25a antigens, but not binding to other antigens of *E. coli*. Optionally, the functionally active variants may further include a potency of complement mediated killing in an SBA assay, and/or optionally further include a potency of an antibody mediated phagocytosis in an OPK assay, and/or optionally further include endotoxin neutralization function in a LAL assay, e.g. with substantially the same biological activity, as determined by the specific binding assay or functional test to target MDR *E. coli*.

For example, the functionally active variants of antibodies 6D1-1B2 and 8A1-1G8 have substantially the same and similar binding affinities as the 8D5-1G10 antibody (see table below).

| 6D1-1B2 | | | 8A1-1G8 | | | 8D5-1G10 | | |
|---|---|---|---|---|---|---|---|---|
| KD (nM) | Kon (1/Ms) | kdis (1/s) | KD (nM) | Kon (1/Ms) | Kdis (1/s) | KD (nM) | Kon (1/Ms) | Kdis (1/s) |
| 0.6 | 8.43E+04 | <5.0E-05 | 4.72 | 4.01E+04 | 1.89E-04 | 1.76 | 4.23E+04 | 7.44E-05 |

The term "substantially the same biological activity" as used herein refers to the activity as indicated by substantially the same activity being at least 50%, at least 60%, at least 70%, at least 80%, at least 90%, at least 95%, at least 98% or even at least 100% or at least 110%, or at least 120%, or at least 130%, or at least 140%, or at least 150%, or at least 160%, or at least 170%, or at least 180%, or at least 190%, e.g. up to 200% of the activity as determined for the parent antibody.

The preferred variants or derivatives as described herein are functionally active with regard to the antigen binding, preferably which have a potency to specifically bind O25b antigen, and not binding to other antigens of *E. coli*, e.g. binding to O25b and not binding to the O25a antigen of *E. coli*, or not significantly binding the O25a antigen, or cross-specifically binding both, O25b and O25 antigens, e.g. preferentially binding the O25b antigen relative to O25a, or binding the O25b with higher affinity as compared to current polyclonal typing sera raised against O25 (O25a) strains. Preferred variants are not binding to other antigens of *E. coli*, with a Kd value difference of at least 2 logs, preferably at least 3 logs, and optionally further including a potency of complement mediated killing in an SBA assay, e.g. to achieve significant reduction in bacterial counts relative to control samples not containing the antibody, and/or optionally further including a potency of an antibody mediated phagocytosis in an OPK assay, such as to achieve significant reduction in bacterial counts relative to control samples not containing the antibody, and/or optionally further including endotoxin neutralization function in a LAL or TLR4 signalling assay, such as to achieve significant reduction in free LPS relative to control samples not containing the antibody, e.g. with substantially the same biological activity, as determined by the specific binding assay or functional test to target MDR *E. coli*. The significant reduction of analytes in the various assays typically means the reduction of at least 50%, preferably at least 60%, 70%, 80%, 90%, 95% or 98% up to complete reduction of about 100% (+/−1%).

In a preferred embodiment the functionally active variant of a parent antibody a) is a biologically active fragment of the antibody, the fragment comprising at least 50% of the sequence of the molecule, preferably at least 60%, at least 70%, at least 80%, at least 90%, or at least 95% and most preferably at least 97%, 98% or 99%;

b) is derived from the antibody by at least one amino acid substitution, addition and/or deletion, wherein the functionally active variant has a sequence identity to the molecule or part of it, such as an antibody of at least 50% sequence identity, preferably at least 60%, more preferably at least 70%, more preferably at least 80%, still more preferably at least 90%, even more preferably at least 95% and most preferably at least 97%, 98% or 99%; and/or c) consists of the antibody or a functionally active variant thereof and additionally at least one amino acid or nucleotide heterologous to the polypeptide or the nucleotide sequence.

In one preferred embodiment of the invention, the functionally active variant of the antibody according to the invention is essentially identical to the variant described above, but differs from its polypeptide or the nucleotide sequence, respectively, in that it is derived from a homologous sequence of a different species. These are referred to as naturally occurring variants or analogs.

The term "functionally active variant" also includes naturally occurring allelic variants, as well as mutants or any other non-naturally occurring variants. As is known in the art, an allelic variant is an alternate form of a (poly) peptide that is characterized as having a substitution, deletion, or addition of one or more amino acids that does essentially not alter the biological function of the polypeptide.

Functionally active variants may be obtained by sequence alterations in the polypeptide or the nucleotide sequence, e.g. by one or more point mutations, wherein the sequence alterations retains a function of the unaltered polypeptide or the nucleotide sequence, when used in combination of the invention. Such sequence alterations can include, but are not limited to, (conservative) substitutions, additions, deletions, mutations and insertions.

Specific functionally active variants are CDR variants. A CDR variant includes an amino acid sequence modified by at least one amino acid in the CDR region, wherein said modification can be a chemical or a partial alteration of the amino acid sequence, which modification permits the variant to retain the biological characteristics of the unmodified sequence. A partial alteration of the CDR amino acid sequence may be by deletion or substitution of one to several amino acids, e.g. 1, 2, 3, 4 or 5 amino acids, or by addition or insertion of one to several amino acids, e.g. 1, 2, 3, 4 or 5 amino acids, or by a chemical derivatization of one to several amino acids, e.g. 1, 2, 3, 4 or 5 amino acids, or combination thereof. The substitutions in amino acid residues may be conservative substitutions, for example, substituting one hydrophobic amino acid for an alternative hydrophobic amino acid.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

A point mutation is particularly understood as the engineering of a polynucleotide that results in the expression of an amino acid sequence that differs from the non-engineered amino acid sequence in the substitution or exchange, deletion or insertion of one or more single (non-consecutive) or doublets of amino acids for different amino acids.

Preferred point mutations refer to the exchange of amino acids of the same polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;
Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).

The "positively" charged amino acids are:

Arginine: (Arg, R) polar, positive; and
Lysine: (Lys, K) polar, positive.

The "negatively" charged amino acids are:

Aspartic acid: (Asp, D) polar, negative; and
Glutamic acid: (Glu, E) polar, negative.

"Percent (%) amino acid sequence identity" with respect to the antibody sequences and homologs described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

An antibody variant is specifically understood to include homologs, analogs, fragments, modifications or variants with a specific glycosylation pattern, e.g. produced by glycoengineering, which are functional and may serve as functional equivalents, e.g. binding to the specific targets and with functional properties.

An antibody of the present invention may or may not exhibit Fc effector function. Preferably the antibody exhibits Fc effector function and is functionally active in an SBA and/or OPK assay. Specific antibodies may be devoid of an active Fc moiety, thus, either composed of antibody domains that do not contain an Fc part of an antibody or that do not contain an Fcgamma receptor binding site, or comprising antibody domains lacking Fc effector function, e.g. by modifications to reduce Fc effector functions. Alternative antibodies may be engineered to incorporate modifications to increase Fc effector functions, in particular to enhance OPK and/or SBA activity.

Such modifications may be effected by mutagenesis, e.g. mutations in the Fcgamma receptor binding site or by derivatives or agents to interfere with ADCC and/or CDC activity of an antibody format, so to achieve reduction or increase of Fc effector function.

A significant reduction of Fc effector function is typically understood to refer to Fc effector function of less than 10% of the unmodified (wild-type) format, preferably less than 5%, as measured by ADCC and/or CDC activity. A significant increase of Fc effector function is typically understood to refer to an increase in Fc effector function of at least 10% of the unmodified (wild-type) format, preferably at least 20%, 30%, 40% or 50%, as measured by ADCC and/or CDC activity.

The term "glycoengineered" variants with respect to antibody sequences shall refer to glycosylation variants having modified immunogenic properties, ADCC and/or CDC as a result of the glycoengineering. All antibodies contain carbohydrate structures at conserved positions in the heavy chain constant regions, with each isotype possessing a distinct array of N-linked carbohydrate structures, which variably affect protein assembly, secretion or functional activity. IgG1 type antibodies are glycoproteins that have a conserved N linked glycosylation site at Asn297 in each CH2 domain. The two complex bi-antennary oligosaccharides attached to Asn297 are buried between the CH2 domains, forming extensive contacts with the polypeptide backbone, and their presence is essential for the antibody to mediate effector functions such as antibody dependent complement mediated bacterial killing or uptake by phagocytic cells. Removal of N-Glycan at N297, e.g. through mutating N297, e.g. to A, or T299 typically results in aglycosylated antibody formats with reduced effector function.

Major differences in antibody glycosylation occur between cell lines, and even minor differences are seen for a given cell line grown under different culture conditions. Expression in bacterial cells typically provides for an aglycosylated antibody. CHO cells with tetracycline-regulated expression of β(1,4)-N-acetylglucosaminyltransferase III (GnTIII), a glycosyltransferase catalyzing formation of bisecting GlcNAc, was reported to have improved functional (ADCC) activity (Umana et al., 1999, Nature Biotech. 17:176-180). In addition to the choice of host cells, factors that affect glycosylation during recombinant production of antibodies include growth mode, media formulation, culture density, oxygenation, pH, purification schemes and the like.

The term "antigen-binding site" or "binding site" refers to the part of an antibody that participates in antigen binding. The antigen binding site is formed by amino acid residues of the N-terminal variable ("V") regions of the heavy ("H") and/or light ("L") chains, or the variable domains thereof. Three highly divergent stretches within the V regions of the heavy and light chains, referred to as "hypervariable regions", are interposed between more conserved flanking stretches known as framework regions, The antigen-binding site provides for a surface that is complementary to the three-dimensional surface of a bound epitope or antigen, and the hypervariable regions are referred to as "complementarity-determining regions", or "CDRs." The binding site incorporated in the CDR is herein also called "CDR binding site".

The term "antigen" as used herein interchangeably with the terms "target" or "target antigen" shall refer to a whole target molecule or a fragment of such molecule recognized by an antibody binding site. Specifically, substructures of an antigen, e.g. a polypeptide or carbohydrate structure, generally referred to as "epitopes", e.g. B-cell epitopes or T-cell epitope, which are immunologically relevant, may be recognized by such binding site. Specific antigens like the O25b or O25a antigens are provided as isolated antigens, or else in the form of *E. coli* cells or cell fractions.

The term "epitope" as used herein shall in particular refer to a molecular structure which may completely make up a specific binding partner or be part of a specific binding partner to a binding site of an antibody. An epitope may either be occurring in nature or artificial, and composed of a carbohydrate, a peptidic structure, a fatty acid, an organic, biochemical or inorganic substance or derivatives thereof and any combinations thereof. If an epitope is comprised in a peptidic structure, such as a peptide, a polypeptide or a protein, it will usually include at least 3 amino acids, preferably 5 to 40 amino acids, and more preferably between about 10-20 amino acids. Epitopes can be either linear or conformational epitopes. A linear epitope is comprised of a single segment of a primary sequence of a polypeptide or carbohydrate chain. Linear epitopes can be contiguous or overlapping. Conformational epitopes are comprised of amino acids or carbohydrates brought together by folding the polypeptide to form a tertiary structure and the amino acids are not necessarily adjacent to one another in the linear sequence. Specifically and with regard to polypeptide antigens a conformational or discontinuous epitope is characterized by the presence of two or more discrete amino acid residues, separated in the primary sequence, but assembling to a consistent structure on the surface of the molecule when the polypeptide folds into the native protein/antigen.

Herein the term "epitope" shall particularly refer to the single epitope recognized by an antibody, or the mixture of epitopes comprising epitope variants, each recognized by an antibody specifically recognizing the target, e.g. the epitope specifically recognized by an antibody selected from the group consisting of antibodies designated as 6D1-1B2, 8A1-1G8, 8D5-1G10 and 8D10-C8. Specifically, the epitope targeted by an antibody selected from the group consisting of 6D1-1B2, 8A1-1G8, 8D5-1G10 and 8D10-C8 is a carbohydrate epitope.

The term "expression" is understood in the following way. Nucleic acid molecules containing a desired coding sequence of an expression product such as e.g. an antibody as described herein, and control sequences such as e.g. a promoter in operable linkage, may be used for expression purposes. Hosts transformed or transfected with these sequences are capable of producing the encoded proteins. In order to effect transformation, the expression system may be included in a vector; however, the relevant DNA may also be integrated into the host chromosome. Specifically the term refers to a host cell and compatible vector under suitable conditions, e.g. for the expression of a protein coded for by foreign DNA carried by the vector and introduced to the host cell.

Coding DNA is a DNA sequence that encodes a particular amino acid sequence for a particular polypeptide or protein such as e.g. an antibody. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes.

"Vectors" used herein are defined as DNA sequences that are required for the transcription of cloned recombinant nucleotide sequences, i.e. of recombinant genes and the translation of their mRNA in a suitable host organism.

An "expression cassette" refers to a DNA coding sequence or segment of DNA that code for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct".

Expression vectors comprise the expression cassette and additionally usually comprise an origin for autonomous replication in the host cells or a genome integration site, one or more selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The term "vector" as used herein includes autonomously replicating nucleotide sequences as well as genome integrating nucleotide sequences. A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g. a foreign gene) can be introduced into a host cell, so as to transform the host and promote expression (e.g. transcription and translation) of the introduced sequence.

The term "host cell" as used herein shall refer to primary subject cells transformed to produce a particular recombinant protein, such as an antibody as described herein, and any progeny thereof. It should be understood that not all progeny are exactly identical to the parental cell (due to deliberate or inadvertent mutations or differences in environment), however, such altered progeny are included in these terms, so long as the progeny retain the same functionality as that of the originally transformed cell. The term "host cell line" refers to a cell line of host cells as used for expressing a recombinant gene to produce recombinant polypeptides such as recombinant antibodies. The term "cell line" as used herein refers to an established clone of a particular cell type that has acquired the ability to proliferate over a prolonged period of time. Such host cell or host cell line may be maintained in cell culture and/or cultivated to produce a recombinant polypeptide.

An "immune response" to a composition, e.g. an immunogenic composition, herein also termed "immunogen" comprising an antigen or epitope, or a vaccine as described herein is the development in the host or subject of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

A "protective immune response" is understood as therapeutic immune response and refers to an immune response to an antigen derived from a pathogen, which in some way prevents, ameliorates, treats or at least partially arrests disease symptoms, side effects or progression. Specifically the protective immune response is triggered that provides a significantly better outcome of an induced or natural infection or toxin challenge in comparison to that of the non-immune population.

An immunogen or immunogenic composition usually comprises the antigen or epitope and a carrier, which may specifically comprise an adjuvant. The term "adjuvant" refers to a compound that when administered in conjunction with an antigen augments and/or redirects the immune response to the antigen, but when administered alone does not generate an immune response to the antigen. Adjuvants can augment an immune response by several mechanisms including lymphocyte recruitment, stimulation of B and/or T cells, and stimulation of macrophages. Exemplary carriers are liposomes or cationic peptides; exemplary adjuvants are aluminium phosphate or aluminium hydroxide, MF59 or CpG oligonucleotide.

The term "isolated" or "isolation" as used herein with respect to a nucleic acid, an antibody or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those chemically synthesized.

With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

With reference to polypeptides or proteins, such as antibodies or epitopes of the invention, the term "isolated" shall specifically refer to compounds that are free or substantially free of material with which they are naturally associated such as other compounds with which they are found in their natural environment, or the environment in which they are prepared (e g. cell culture) when such preparation is by recombinant DNA technology practiced in vitro or in vivo. Isolated compounds can be formulated with diluents or adjuvants and still for practical purposes be isolated—for example, the polypeptides or polynucleotides can be mixed with pharmaceutically acceptable carriers or excipients when used in diagnosis or therapy. In particular, the isolated antibody of the invention differs from polyclonal serum preparations raised against O25(a) strains, because it is provided in the isolated and purified form, preferably provided in a preparation comprising the isolated antibody as the only active substance. This does not preclude, however, that the isolated antibody is provided in a combination product comprising a limited number of further well-defined (isolated) antibodies. Isolated antibodies may as well be provided on a solid, semi-liquid or liquid carrier, such as beads.

The term "neutralizing" or "neutralization" is used herein in the broadest sense and refers to any molecule that inhibits a pathogen, such as MDR *E. coli* from infecting a subject, or to inhibit the pathogen from promoting infections by producing potent protein toxins, or to inhibit the toxins from damaging a target cell in a subject, irrespective of the mechanism by which neutralization is achieved. Neutralization can be achieved, e.g., by an antibody that inhibits the binding and/or interaction of the MDR *E. coli* endotoxin with its cognate receptor on target cells (e.g. binding to the TLR4 receptor). Neutralization can further occur by removal of endotoxin molecules from the circulation by Fc mediated functions.

The neutralization potency is typically determined in a standard assay, e.g. LAL test, where the inhibition of endotoxin's biological activity is measured, e.g. by colorimetry.

The term "MDR *E. coli*" is understood in the following way: Infections with multi-drug resistant *E. coli* that are in a significant portion are due to the ST131-O25b:H4 clonal lineage, which emerged only in the last decade and became a globally spread dominant resistant clone. Multi-resistant *E. coli* is particularly understood as those strains demonstrating resistance to three or more classes of antibiotics, e.g. the following agents/groups: penicillins, cephalosporins, carbapenems, aminoglycosides, tetracyclines, fuoroquinolones, nitrofurantoin, trimethoprim (and its combinations), fosfomycin, polymixins, chloramphenicol, azthreonam, tigecycline.

The acidic capsular polysaccharide (CPS) is a thick, mucous-like, layer of polysaccharide that surrounds most pathogen *E. coli*. It is, thus, surprising that the specific epitope recognized by an antibody of the invention would specifically be accessible on both, the encapsulated and the non-encapsulated MDR *E. coli* strain.

Antibodies combating or neutralizing MDR *E. coli* are interfering with the pathogens and pathogenic reactions, thus able to limit or prevent infection and/or to ameliorate a disease condition resulting from such infection, or to inhibit MDR *E. coli* pathogenesis, in particular dissemination and replication into or within sterile body compartments/sites of the host. In this regard "protective antibodies" are understood herein as antibodies that are responsible for immunity to an infectious agent observed in active or passive immunity. In particular, protective antibodies as described herein are possibly used for therapeutic purposes, e.g. for prophylaxis or therapy, to prevent, ameliorate, treat or at least partially arrest disease symptoms, side effects or progression of disease induced by a pathogen. Specifically, protective antibodies are able to kill or impede replication of live *E. coli* cells by e.g. inducing serum bactericidal or opsonophagocytic activities, or remove whole bacterial cells or the LPS molecules thereof from the sterile body sites following therapeutic applications (i.e. given on an established infection). Alternatively, prophylactically applied protective antibodies inhibit establishment of an infection (i.e. spread of *E. coli* from non-sterile sites to sterile body compartments) by one of the abovementioned or other mechanisms.

The term "O25b antigen" is herein understood as the LPS O-antigen with structure elucidated in example 2 and FIG. 3 (*a*). The structure is similar, but distinct from that of the O25(a) antigen. O25b is herein understood as a serotype, which is similar, but distinct from O25a (see FIG. 3 (*a*)).

The term "O25 antigen" is herein understood as the antigen made of the pentasaccharide repeating unit described by Kenne et al. (Kenne L, Lindberg B, Madden J K, Lindberg A A, Gemski P Jr. Structural studies of the *Escherichia coli* O-antigen 25. Carbohydr Res. 28; 122(2): 249-56, 1983). Before identifying the O25b antigen, the term O25 has stood for O25a as described herein (see FIG. 3 (*b*)).

The term "O25a antigen" is herein understood as a synonym for O25 antigen.

The term "recombinant" as used herein shall mean "being prepared by or the result of genetic engineering". A recombinant host specifically comprises an expression vector or cloning vector, or it has been genetically engineered to contain a recombinant nucleic acid sequence, in particular employing nucleotide sequence foreign to the host. A recombinant protein is produced by expressing a respective recombinant nucleic acid in a host. The term "recombinant antibody", as used herein, includes antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant antibodies comprise antibodies engineered to include rearrangements and mutations which occur, for example, during antibody maturation.

As used herein, the term "specificity" or "specific binding" refers to a binding reaction which is determinative of the cognate ligand of interest in a heterogeneous population of molecules. Thus, under designated conditions (e.g. immunoassay conditions), an antibody specifically binds to its particular target and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10 fold different (understood as at least 1 log difference), preferably the difference is at least 100 fold (understood as at least 2 logs difference), and more preferred a least 1000 fold (understood as at least 3 logs difference). The term "specificity" or "specific binding" is also understood to apply to binders which bind to one or more molecules, e.g. cross-specific binders.

The antibody of the invention specifically is selective in only binding the O25b antigen, or preferentially binding the O25b antigen relative to the O25a antigen, or binding the O25b with higher affinity as compared to polyclonal serum raised against O25a strains, which serum binds to the O25b antigen with a low affinity. Thus, the antibody of the invention may be understood to differentially bind those antigens, e.g. at least with equal affinity, or more than equal affinity, such as with a different affinity with a Kd difference of at least 1 log, preferably at least 2 logs, more preferably at least 3 logs. Such antibody selectively binding to the O25b antigen relative to the O25a antigen is preferably used for diagnostic or therapeutic purposes. For some diagnostic purposes an antibody is specifically used which only binds the O25b antigen in a detectable manner.

Use of the term "having the same specificity", "having the same binding site" or "binding the same epitope" indicates that equivalent monoclonal antibodies exhibit the same or essentially the same, i.e. similar immunoreaction (binding) characteristics and compete for binding to a pre-selected target binding sequence. The relative specificity of an antibody molecule for a particular target can be relatively determined by competition assays, e.g. as described in Harlow, et al., ANTIBODIES: A LABORATORY MANUAL, Cold Spring Harbor Laboratory Press, Cold Spring Harbor, N.Y., 1988).

The term "subject" as used herein shall refer to a warm-blooded mammalian, particularly a human being. In particular the medical use of the invention or the respective method of treatment applies to a subject in need of prophylaxis or treatment of a disease condition associated with a MDR *E. coli* infection or suffering from disease, including early stage or late stage disease. The term "patient" includes human and other mammalian subjects that receive either prophylactic or therapeutic treatment. The term "treatment" is thus meant to include both prophylactic and therapeutic treatment.

A subject is e.g. treated for prophylaxis or therapy of MDR *E. coli* disease conditions. In particular, the subject is treated, which is either at risk of infection or developing such disease or disease recurrence, or a subject that is suffering from such infection and/or disease associated with such infection.

Specifically the term "prophylaxis" refers to preventive measures which is intended to encompass prevention of the onset of pathogenesis or prophylactic measures to reduce the risk of pathogenesis.

Specifically, the method for treating, preventing, or delaying a disease condition in a subject as described herein, is by interfering with the pathogenesis of MDR *E. coli* as causal agent of the condition.

The term "substantially pure" or "purified" as used herein shall refer to a preparation comprising at least 50% (w/w), preferably at least 60%, 70%, 80%, 90% or 95% of a compound, such as a nucleic acid molecule or an antibody. Purity is measured by methods appropriate for the compound (e.g. chromatographic methods, polyacrylamide gel electrophoresis, HPLC analysis, and the like).

The term "therapeutically effective amount", used herein interchangeably with any of the terms "effective amount" or "sufficient amount" of a compound, e.g. an antibody or immunogen of the present invention, is a quantity or activity sufficient to, when administered to the subject effect beneficial or desired results, including clinical results, and, as such, an effective amount or synonym thereof depends upon the context in which it is being applied.

An effective amount is intended to mean that amount of a compound that is sufficient to treat, prevent or inhibit such diseases or disorder. In the context of disease, therapeutically effective amounts of the antibody as described herein are specifically used to treat, modulate, attenuate, reverse, or affect a disease or condition that benefits from an inhibition of MDR *E. coli* pathogenesis, for example, adhesion and colonization of mucosal surfaces, uncontrolled replication within sterile body sites, and toxicity of host cells by bacterial products.

The amount of the compound that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

The antibody or the immunogen of the present invention may be used prophylactically to inhibit onset of MDR *E. coli* infection, or therapeutically to treat MDR *E. coli* infection, particularly MDR *E. coli* infections that are known to be refractory or in the case of the specific subject, have proven refractory to treatment with other conventional antibiotic therapy.

A therapeutically effective amount of the antibody as described herein, such as provided to a human patient in need thereof, may specifically be in the range of 0.5-500 mg, preferably 1-400 mg, even more preferred up to 300 mg, up to 200 mg, up to 100 mg or up to 10 mg, though higher doses may be indicated e.g. for treating acute disease conditions.

Moreover, a treatment or prevention regime of a subject with a therapeutically effective amount of the antibody of the present invention may consist of a single administration, or alternatively comprise a series of applications. For example, the antibody may be administered at least once a year, at least once a half-year or at least once a month. However, in another embodiment, the antibody may be administered to the subject from about one time per week to about a daily administration for a given treatment. The length of the treatment period depends on a variety of factors, such as the severity of the disease, either acute or chronic disease, the age of the patient, the concentration and the activity of the antibody format. It will also be appreciated that the effective dosage used for the treatment or prophylaxis may increase or decrease over the course of a particular treatment or prophylaxis regime. Changes in dosage may result and become apparent by standard diagnostic assays known in the art. In some instances, chronic administration may be required.

An effective amount of an immunogen as described herein, such as provided to a patient at risk of developing a disease condition associated with an MDR E. coli infection, may specifically be in the range of 1-15 mg/kg per dose.

For example the immunogen may be administered as a first dose followed by one or more booster dose(s), within a certain timeframe, according to a prime-boost immunization scheme to induce a long-lasting, efficacious immune response to an MDR E. coli infection. A preferred vaccination schedule would encompass administration of three doses, e.g. a first dose on day 0, a second dose on day 5-40, and a third dose on day 10-100, preferably on days 0, 28 and 90. According to a preferred accelerated schedule the administration may be on days 0, 7 and 14. Accelerated schedules may be indicated for prophylaxis, e.g. for patients facing elective surgery. Usually alum is used as an adjuvant, e.g. as phosphate or hydroxide.

Therefore, the present subject matter is based on the discovery of murine mAbs highly specific to O25b. These antibodies have great potential as diagnostic reagents for the identification of MDR strains belonging to the ST131 lineage. Furthermore, in particular following humanization, these mAbs are suitable to be used for the prophylaxis (e.g. for high risk groups) and treatment of E. coli infections caused by ST131-O25b:H4 strains.

The O25b and O25 (O25a) carbohydrate antigens were thought to be identical or very similar based on the fact that immune serum against O25 is routinely used in the diagnostic identification of E. coli strains expressing O25b antigens. The genetic background of O-antigen synthesis in ST131 strains is not fully elucidated, however, a specific gene within the rfb cluster (encoding O-antigen synthesis) forms the basis of PCR based identification of O25b strains. Furthermore, no structural data supported any difference between O25(a) and O25b antigens so far.

It was, thus, surprising that an antibody of invention could specifically bind the O25b antigen, and specifically differentiate between O25b and O25a antigens.

In order to confirm the genetic difference between O25b and O25a antigen expressing E. coli strains, the rfb cluster encoding O-antigen synthesis was sequenced from a commercially available strain 81009 (Szijarto et al, FEMS Microbiol Lett, 2012, 332:131-6) using a primer walk method starting with oligonucleotides specific to conserved flanking genes: gnd and galF. The resulting contig of the rfb operon is 11,300 bp long and only partially homologous to that encoding the O25 antigen synthesis enzymes (NCBI accession number GU014554). It turned out that a 2043 bp long segment at the 3' end of the O25b rfb operon is non-homologous to the corresponding region of the O25 rfb operon, where this segment is replaced by a 6267 bp long sequence encoding fucose synthesis amd transport.

The structure of the O-specific PS biological repeating unit (RU) present in LPS isolated from E. coli ST131 was analysed in details in a purified fraction built up by the core OS substituting with one repeating unit (RU). The RU of the LPS ST131 is an O-acetylated pentasaccharide with the structure depicted on FIG. 3.

In fact, the RU structure of the ST131 O-PS differs from the LPS O25 RU reported by Kenne et al. (Kenne, Lindberg et al., Carbohydr Res. 1983 Oct. 28; 122(2):249-56) and to the best of our knowledge it is a new O-serotype among E. coli lipopolysaccharides (Stenutz et al. FEMS Microbiol Rev. 2006 May; 30(3):382-403. Review). Additionally, preliminary results of MALDI-TOF mass spectrometry and composition analyses (sugar and methylation analyses) of a core oligosaccharide isolated from LPS ST131 supported K-12 type, what was previously reported by Szijártó V. et al. on the basis of genetic analyses (Szijarto et al, FEMS Microbiol Lett, 2012, 332:131-6). It was shown that LPS ST131 is consisted of two main core oligosaccharides (OS) glycoforms. The type of glycoform is dependent on the presence or absence of the O-specific polysaccharide (PS). Prevailing glycoform of the unsubstituted core OS is truncated version of K-12 core oligosaccharide, which is devoid of →7)-α-Hepp-(1→6)-α-Glcp disaccharide. Presence of that disaccharide is the difference between O-PS substituted core OS and nonsubstituted core OS.

According to a specific aspect, there is provided an antibody selectively binding the O25b specific epitope, e.g. binding the same epitope as the 8D5-1G10 antibody or any of the antibodies designated as 6D1-1B2 or 8A1-1G8, or the 8D10-C8 antibody, which term includes variants binding to essentially the same epitope; or comprising the same binding site as the 8D5-1G10 antibody or any of the antibodies designated as 6D1-1B2 or 8A1-1G8, or the 8D10-C8 antibody, which term includes variants comprising essentially the same binding site. The antibodies designated as 6D1-1B2, 8A1-1G8, 8D5-1G10 would particularly comprise a binding site specifically differentiating between the O25b antigen and the O25a antigen, and binding only the O25b antigen. The antibody designated as 8D10-C8 would particularly comprise a binding site cross-specifically binding the O25b and O25a antigens, and preferentially binding the O25b antigen as compared to the O25a antigen.

Antibodies are said to "bind to the same epitope" or "comprising the same binding site" or have "essentially the same binding" characteristics, if the antibodies cross-compete so that only one antibody can bind to the epitope at a given point of time, i.e. one antibody prevents the binding or modulating effect of the other.

The term "compete" or "cross-compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope, whether to the same, greater, or lesser extent, the antibodies are said to "cross-compete" with each other for binding of their respective epitope(s). Both competing and cross-competing antibodies are encompassed by the present invention.

Competition herein means a greater relative inhibition than about 30% as determined by competition ELISA analysis, e.g. as described in the Examples section. It may be desirable to set a higher threshold of relative inhibition as criteria of what is a suitable level of competition in a particular context, e.g., where the competition analysis is used to select or screen for new antibodies designed with the intended function of the binding of O25b. Thus, for example, it is possible to set criteria for the competitive binding, wherein at least 40% relative inhibition is detected, or at least 50%, at least 60%, at least 70%, at least 80%, at least 90% or even at least 100%, before an antibody is considered sufficiently competitive.

Specifically, there is provided an antibody comprising the variable region of any of the antibodies designated as 6D1-1B2, 8A1-1G8, 8D5-1G10, or 8D10-C8, in particular at least one of the CDR sequences, preferably at least two, at least 3, at least 4, at least 5 or at least six of the CDR sequences of an antibody selected from the group consisting of 6D1-1B2, 8A1-1G8, 8D5-1G10 and 8D10-C8 antibodies, or CDR variants thereof which are functionally active. More specifically, there is provided any of the antibodies designated as 6D1-1B2, 8A1-1G8, 8D5-1G10, or 8D10-C8.

Specifically, the antibody designated as 8D5-1G10 antibody or 8D10-C8 antibody, or any functionally active variant thereof may be produced employing the deposited material or the respective nucleotide sequence contained therein, such as one of the plasmids and/or one of the deposited host cells.

According to a specific aspect, the 8D5-1G10 antibody or a functionally equivalent variant thereof may be derived from an antibody comprising a variable region encoded by any of the plasmids incorporated in the deposited host cells under DSM 26763 and/or DSM 26762; e.g. employing a partial or (point) mutated CDR sequence of the deposited material to engineer the specific antibody or any functionally active variant thereof.

According to a further specific aspect, the 8D5-1G10 antibody or a functionally equivalent variant thereof may be derived from or employing the variable region of an antibody produced by a host cell deposited under DSM 26763 and/or DSM 26762; e.g. employing a partial sequence, e.g. one or more of the CDR sequences, of the deposited material to engineer the specific antibody or any functionally active variant thereof.

Specifically, the 6D1-1B2 or 8A1-1G8 antibody variant is a CDR variant of the 8D5-1G10 antibody that is functionally active, e.g. with partial alterations in at least one of the CDR sequences.

According to a specific aspect, the 8D10-C8 antibody or a functionally equivalent variant thereof may be derived from an antibody comprising a variable region encoded by any of the plasmids incorporated in the deposited host cells under DSM 28171 and/or DSM 28172; e.g. employing a partial or (point) mutated CDR sequence of the deposited material to engineer the specific antibody or any functionally active variant thereof.

According to a further specific aspect, the 8D10-C8 antibody or a functionally equivalent variant thereof may be derived from or employing the variable region of an antibody produced by a host cell deposited under DSM 28171 and/or DSM 28172; e.g. employing a partial sequence, e.g. one or more of the CDR sequences, of the deposited material to engineer the specific antibody or any functionally active variant thereof.

In certain aspects, the invention provides for such variant antibodies, preferably monoclonal antibodies, most preferably murine, humanized or human antibodies, comprising a heavy chain and a light chain, wherein any of the heavy chain or VH variable region or the respective CDRs comprises an amino acid sequence as derived from the respective deposited plasmid and/or from the respective deposited host cell.

In certain aspects, the invention provides for such variant antibodies, preferably monoclonal antibodies, most preferably murine, humanized or human antibodies, comprising a heavy chain and a light chain, wherein any of the light chain or VL variable region or the respective CDRs comprises an amino acid sequence as derived from the respective deposited plasmid and/or from the respective deposited host cell.

In certain aspects, the invention provides for such variant antibodies, preferably monoclonal antibodies, most preferably murine, humanized or human antibodies, comprising a heavy chain and a light chain, wherein any of the heavy and light chain, or the VH/VL variable regions, or the respective CDRs comprises an amino acid sequence as derived from the respective deposited plasmids and/or from the respective deposited host cells.

In certain aspects, the invention also provides for such variant antibodies, comprising the respective binding sequences, such as the variable sequences and/or the CDR sequences, as derived from the deposited material, wherein the binding sequences, e.g. any CDR sequence, comprises a sequence that has at least 60%, at least 70%, or at least 80%, or at least 90%, or at least 95%, or at least 99% identity to the amino acid sequence as derived from the deposited material, and wherein the variant is a functionally active variant.

As described herein, in one aspect the invention provides antibody molecules characterized by, e.g. the ability to compete with monoclonal antibody 8D5-1G10 or 8D10-C8 for binding to the O25b antigen. Any of the 6D1-1B2, 8A1-1G8, 8D5-1G10, antibodies is a murine IgG3 antibody and 8D10-C8 antibody is a murine IgG2b antibody which carries kappa light chains, which the inventors isolated and characterized. The variable domains of the 8D5-1G10 antibody or the 8D10-C8 antibody are expressed by the deposited material as referenced herein. Thus, the binding characteristics as determined by the light chain and heavy chain, and the VL/VH domains of the 8D5-1G10 antibody or the 8D10-C8 antibody are fully disclosed herewith, enabling its use as a parent antibody or the comparison with functionally active variants or competing antibodies of the invention.

The mature variable domain of the heavy chain of 8D5-1G10 (8D5-1G10-HC) is e.g. produced employing the host cell of DSM 26762, or the respective sequence information of the encoding plasmid incorporated therein.

The mature variable domain of the light chain of 8D5-1G10 (8D5-1G10-LC) is e.g. produced employing the host cell of DSM 26763, or the respective sequence information of the encoding plasmid incorporated therein.

The mature variable domain of the heavy chain of 8D10-C8 (8D10-C8-HC) is e.g. produced employing the host cell of DSM 28172, or the respective sequence information of the encoding plasmid incorporated therein.

The mature variable domain of the light chain of 8D10-C8 (8D10-C8-LC) is e.g. produced employing the host cell of DSM 28171, or the respective sequence information of the encoding plasmid incorporated therein.

The differential binding affinity to preferably bind the O25b antigen relative to other *E. coli* antigens, e.g. any carbohydrate antigens other than O25 antigen or any core antigens, is preferably at least 10-fold higher, i.e. with a Kd difference of at least 10, preferably at least 100-fold higher, more preferred at least 1000 fold higher.

The differential binding affinity to preferentially bind the O25b antigen is specifically at least 5 fold, or at least 6-fold, or at least 7-fold, or at least 8-fold, or at least 9-fold, or at least 10-fold higher, in comparison to commercial typing serum, such as the high titer *E. coli* O25 antiserum from Statens Serum Institut (#81369).

The differential binding affinity to preferentially bind the O25b antigen relative to the O25a antigen is specifically at least equal or more than equal, e.g. at least 1.5 fold, or at least 2-fold, or at least 3-fold, or at least 4-fold, or at least 5 fold, or at least 6-fold, or at least 7-fold, or at least 8-fold, or at least 9-fold, or at least 10-fold higher.

Preferred antibodies of the invention are binding any of said individual antigens, in particular the O25b antigen, with a high affinity, in particular with a high on and/or a low off rate, or a high avidity of binding. The binding affinity of an antibody is usually characterized in terms of the concentration of the antibody, at which half of the antigen binding sites are occupied, known as the dissociation constant (Kd, or KD). Usually a binder is considered a high affinity binder with a $Kd<10^{-7}$ M, in some cases, e.g. for therapeutic purposes with higher affinities, e.g. with a $Kd<10^{-8}$ M, preferably a $Kd<10^{-9}$ M, even more preferred is a $Kd<10^{-10}$ M.

Yet, in a particularly preferred embodiment the individual antigen binding affinities are of medium affinity, e.g. with a Kd of less than $10^{-6}$ and up to $10^{-7}$ M, e.g. when binding to at least two antigens.

Medium affinity binders may be provided according to the invention, preferably in conjunction with an affinity maturation process, if necessary.

Affinity maturation is the process by which antibodies with increased affinity for a target antigen are produced. With structural changes of an antibody, including amino acid mutagenesis or as a consequence of somatic mutation in immunoglobulin gene segments, variants of a binding site to an antigen are produced and selected for greater affinities. Affinity matured antibodies may exhibit a several logfold greater affinity than a parent antibody. Single parent antibodies may be subject to affinity maturation. Alternatively pools of antibodies with similar binding affinity to the target antigen may be considered as parent structures that are varied to obtain affinity matured single antibodies or affinity matured pools of such antibodies.

The preferred affinity matured variant of an antibody according to the invention exhibits at least a 10 fold increase in affinity of binding, preferably at least a 100 fold increase. The affinity maturation may be employed in the course of the selection campaigns employing respective libraries of parent molecules, either with antibodies having medium binding affinity to obtain the antibody of the invention having the specific target binding property of a binding affinity $Kd<10^{-7}$ M. Alternatively, the affinity may be even more increased by affinity maturation of the antibody according to the invention to obtain the high values corresponding to a Kd of less than $10^{-8}$ M or less than $10^{-9}$ M, preferably less than $10^{-10}$ M or even less than $10^{-11}$ M, most preferred in the picomolar range.

A specific aspect refers to an antibody of the invention characterized by a specific anti-bacterial functional activity, such as complement mediated bacterial killing and opsonophagocytic uptake and killing.

Phagocytic effector cells may be activated through another route employing activation of complement. Antibodies that bind to surface antigens on microorganisms attract the first component of the complement cascade with their Fc region and initiate activation of the "classical" complement system. This results in the stimulation of phagocytic effector cells, which ultimately kill the target bacteria by complement and antibody dependent mechanisms (CDC).

According to a specific embodiment, the antibody of the invention has a cytotoxic activity in the presence of immune-effector cells as measured in a standard SBA or OPK assay. A cytotoxic activity as determined by either of an SBA or OPK assay may be shown for an antibody of the invention, if there is a significant increase in the percentage of bacterial killing as compared to a control. The bactericidal activity related to SBA or OPK is preferably measured as the absolute percentage increase, which is preferably higher than 5%, more preferably higher than 10%, even more preferred higher than 20%, 30%, 40% or 50%.

Antibodies of the present invention may be identified or obtained employing a hybridoma method. In such method, a mouse or other appropriate host animal, such as a hamster, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

For example, the antibodies of the present invention may be obtained from source (parent) antibodies, e.g. obtained by immunizing mice with a non-encapsulated mutant of a representative ST131-O25b:H4 strain 81009 (e.g. 81009Δkps::kan) by replacing the kps cluster (encoding capsular synthesis) with a cassette encoding kanamycin resistance. Serum samples obtained from the mice may then be analyzed, and the spleen of the mouse showing the highest IgG titer against O25b antigen (in ELISA and Western Blot) may be used for hybridoma generation. Following sub-cloning, hybridoma clones may be selected, which secreted antibodies specific to O25b antigens as well as bound to the surface of live wild-type *E. coli* strains expressing O25b antigens. These mAbs may then be purified from hybridoma supernatants for further testing for its specific binding of O25b antigen and possibly for its differential binding affinity to preferentially bind O25b antigen relative to O25a antigen, and engineering of antibodies, e.g. for different diagnostic or therapeutic purposes.

Differentially binding antibodies, herein also called selective antibodies, in some instances, emerge through screening against single antigens. To increase the likelihood of isolating differentially binding clones one would apply multiple selective pressures by processively screening against the different antigens. Special mAb selection strategies employ the O25b and O25a components or other *E. coli* antigens in an alternating fashion.

The recombinant antigen(s) may be used for selecting antibodies from an antibody library, e.g. a yeast-displayed antibody library.

In either event, selective binding can be further improved by antibody optimization methods known in the art. For example, certain regions of the variable regions of the immunoglobulin chains described herein may be subjected to one or more optimization strategies, including light chain shuffling, destinational mutagenesis, CDR amalgamation, and directed mutagenesis of selected CDR and/or framework regions.

Screening methods for identifying antibodies with the desired selective binding properties may be done by display technologies (using phage, bacterial, yeast or mammalian cells). Reactivity can be assessed based on ELISA, Western blotting or surface staining with flow cytometry, e.g. using standard assays.

Once differentially binding antibodies with the desired properties have been identified, the dominant epitope or epitopes recognized by the antibodies may be determined. Methods for epitope mapping are well-known in the art and are disclosed, for example, in *Epitope Mapping: A Practical Approach*, Westwood and Hay, eds., Oxford University Press, 2001.

Epitope mapping concerns the identification of the epitope to which an antibody binds. There are many methods known to those of skill in the art for determining the location of epitopes on proteins, including crystallography analysis of the antibody-antigen complex, competition assays, gene fragment expression assays, and synthetic peptide-based assays. An antibody that "binds the same epitope" as a reference antibody is herein understood in the following way. When two antibodies recognize epitopes that are identical or sterically overlapping epitopes, the antibodies are referred to as binding the same or essentially the same or substantially the same epitopes. A commonly used method for determining whether two antibodies bind to identical or sterically overlapping epitopes is the competition assay, which can be configured in all number of different formats, using either labeled antigen or labeled antibody. Usually, an antigen is immobilized on a 96-well plate, and the ability of unlabeled antibodies to block the binding of labeled antibodies is measured using radioactive or enzyme labels.

Once antibodies with the desired differentially binding properties are identified, such antibodies, including antibody fragments can be produced by methods well-known in the art, including, for example, hybridoma techniques or recombinant DNA technology.

Recombinant monoclonal antibodies can, for example, be produced by isolating the DNA encoding the required antibody chains and transfecting a recombinant host cell with the coding sequences for expression, using well known recombinant expression vectors, e.g. the plasmids of the invention or expression cassette(s) comprising the nucleotide sequences encoding the antibody sequences. Recombinant host cells can be prokaryotic and eukaryotic cells, such as those described above.

According to a specific aspect, the nucleotide sequence may be used for genetic manipulation to humanize the antibody or to improve the affinity, or other characteristics of the antibody. For example, the constant region may be engineered to more nearly resemble human constant regions to avoid immune response, if the antibody is used in clinical trials and treatments in humans. It may be desirable to genetically manipulate the antibody sequence to obtain greater affinity to the target O25b and greater efficacy against MDR *E. coli*. It will be apparent to one of skill in the art that one or more polynucleotide changes can be made to the antibody and still maintain its binding ability to the target O25b.

The production of antibody molecules, by various means, is generally well understood. U.S. Pat. No. 6,331,415 (Cabilly et al.), for example, describes a method for the recombinant production of antibodies where the heavy and light chains are expressed simultaneously from a single vector or from two separate vectors in a single cell. Wibbenmeyer et al., (1999, Biochim Biophys Acta 1430(2):191-202) and Lee and Kwak (2003, J. Biotechnology 101:189-198) describe the production of monoclonal antibodies from separately produced heavy and light chains, using plasmids expressed in separate cultures of *E. coli*. Various other techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

If desired, the antibody of the invention, e.g. the 8D5-1G10 antibody or the 8D10-C8 antibody, or the respective binding site or CDR may be sequenced and the polynucleotide sequence or a sequence variant or mutant thereof may then be cloned into a vector for expression or propagation. The sequence encoding the antibody may be maintained in vector in a host cell and the host cell can then be expanded and frozen for future use. Production of recombinant monoclonal antibodies in cell culture can be carried out through cloning of antibody genes from B cells by means known in the art.

In another aspect, the invention provides an isolated nucleic acid comprising a sequence that codes for production of the recombinant antibody of the present invention.

In another aspect, the invention provides an isolated nucleic acid comprising a sequence that codes for production of the recombinant epitope of the present invention, or a molecule comprising such epitope of the present invention. However, the epitope of the invention may also be synthetically produced, e.g. through any of the synthesis methods well-known in the art.

An antibody or epitope encoding nucleic acid can have any suitable characteristics and comprise any suitable features or combinations thereof. Thus, for example, an antibody or epitope encoding nucleic acid may be in the form of DNA, RNA, or a hybrid thereof, and may include non-naturally-occurring bases, a modified backbone, e.g., a phosphothioate backbone that promotes stability of the nucleic acid, or both. The nucleic acid advantageously may be incorporated in an expression cassette, vector or plasmid of the invention, comprising features that promote desired expression, replication, and/or selection in target host cell (s). Examples of such features include an origin of replication component, a selection gene component, a promoter component, an enhancer element component, a polyadenylation sequence component, a termination component, and the like, numerous suitable examples of which are known.

The present disclosure further provides the recombinant DNA constructs comprising one or more of the nucleotide sequences described herein. These recombinant constructs are used in connection with a vector, such as a plasmid, phagemid, phage or viral vector, into which a DNA molecule encoding any disclosed antibody is inserted.

Monoclonal antibodies are produced using any method that produces antibody molecules by continuous cell lines in culture. Examples of suitable methods for preparing monoclonal antibodies include the hybridoma methods of Kohler et al. (1975, Nature 256:495-497) and the human B-cell hybridoma method (Kozbor, 1984, J. Immunol. 133:3001; and Brodeur et al., Monoclonal Antibody Production Techniques and Applications pp 51-63 (Marcel Dekker, Inc., 1987)).

The invention moreover provides pharmaceutical compositions which comprise an antibody or an immunogen as described herein and a pharmaceutically acceptable carrier or excipient. These pharmaceutical compositions can be administered in accordance with the present invention as a bolus injection or infusion or by continuous infusion. Pharmaceutical carriers suitable for facilitating such means of administration are well known in the art.

Pharmaceutically acceptable carriers generally include any and all suitable solvents, dispersion media, coatings, antibacterial and antifungal agents, isotonic and absorption delaying agents, and the like that are physiologically compatible with an antibody or related composition or combination provided by the invention. Further examples of pharmaceutically acceptable carriers include sterile water, saline, phosphate buffered saline, dextrose, glycerol, ethanol, and the like, as well as combinations of any thereof.

In one such aspect, an antibody can be combined with one or more carriers appropriate a desired route of administration, antibodies may be, e.g. admixed with any of lactose, sucrose, starch, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, polyvinyl alcohol, and optionally further tabletted or encapsulated for conventional administration. Alternatively, an antibody may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other carriers, adjuvants, and modes of administration are well known in the pharmaceutical arts. A carrier may include a controlled release material or time delay material, such as glyceryl monostearate or glyceryl distearate alone or with a wax, or other materials well known in the art.

Additional pharmaceutically acceptable carriers are known in the art and described in, e.g. REMINGTON'S PHARMACEUTICAL SCIENCES. Liquid formulations can be solutions, emulsions or suspensions and can include excipients such as suspending agents, solubilizers, surfactants, preservatives, and chelating agents.

Pharmaceutical compositions are contemplated wherein an antibody or immunogen of the present invention and one or more therapeutically active agents are formulated. Stable formulations of the antibody or immunogen of the present invention are prepared for storage by mixing said immunoglobulin having the desired degree of purity with optional pharmaceutically acceptable carriers, excipients or stabilizers, in the form of lyophilized formulations or aqueous solutions. The formulations to be used for in vivo administration are specifically sterile, preferably in the form of a sterile aqueous solution. This is readily accomplished by filtration through sterile filtration membranes or other methods. The antibody and other therapeutically active agents disclosed herein may also be formulated as immunoliposomes, and/or entrapped in microcapsules.

Administration of the pharmaceutical composition comprising an antibody or immunogen of the present invention, may be done in a variety of ways, including orally, subcutaneously, intravenously, intranasally, intraotically, transdermally, mucosal, topically, e.g., gels, salves, lotions, creams, etc., intraperitoneally, intramuscularly, intrapulmonary, e.g. employing inhalable technology or pulmonary delivery systems, vaginally, parenterally, rectally, or intraocularly.

Examplary formulations as used for parenteral administration include those suitable for subcutaneous, intramuscular or intravenous injection as, for example, a sterile solution, emulsion or suspension.

In one embodiment, the antibody or immunogen of the present invention is the only therapeutically active agent administered to a subject, e.g. as a disease modifying or preventing monotherapy.

Alternatively, the antibody or immunogen of the present invention is administered in combination with one or more other therapeutic or prophylactic agents, including but not limited to standard treatment, e.g. antibiotics, steroid and non-steroid inhibitors of inflammation, and/or other antibody based therapy, e.g. employing anti-bacterial or anti-inflammatory agents.

A combination therapy is particularly employing a standard regimen, e.g. as used for treating MDR *E. coli* infection. This may include antibiotics, e.g. tygecycline, linezolide, methicillin and/or vancomycin.

In a combination therapy, the antibody may be administered as a mixture, or concomitantly with one or more other therapeutic regimens, e.g. either before, simultaneously or after concomitant therapy.

Prophylactic administration of immunogens in some cases may employ a vaccine comprising the immunogen of the present invention, i.e. a monovalent vaccine. Yet, a multivalent vaccine comprising different immunogens to induce an immune response against the same or different target pathogens may be used.

The biological properties of the antibody, the immunogen or the respective pharmaceutical preparations of the invention may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the antibody to be used as a therapeutic or as a prophylactic with the appropriate half-life, effector function, (cross-) neutralizing activity and/or immune response upon active or passive immunotherapy. Any organism, preferably mammals, may be used for testing. For example because of their genetic similarity to humans, primates, monkeys can be suitable therapeutic models, and thus may be used to test the efficacy, toxicity, pharmacokinetics, pharmacodynamics, half-life, or other property of the subject agent or composition. Tests in humans are ultimately required for approval as drugs, and thus of course these experiments are contemplated. Thus, the antibody, immunogen and respective pharmaceutical compositions of the present invention may be tested in humans to determine their therapeutic or prophylactic efficacy, toxicity, immunogenicity, pharmacokinetics, and/or other clinical properties.

The invention also provides the subject antibody of the invention for diagnostic purposes, e.g. for use in methods of detecting and quantitatively determining the concentration of a bacterial load or antibody as immunoreagent or target in a biological fluid sample.

The invention also provides methods for detecting the degree of sepsis or MDR *E. coli* infection in a biological sample, e.g. the load of a sample with MDR *E. coli*, such as a body fluid, comprising the step of contacting the sample with an antibody of the invention. The antibody of the invention may be employed in any known assay method, such as competitive binding assays, direct and indirect sandwich assays, immunoprecipitation assays and enzyme-linked immunosorbent assays (ELISA).

The preferred diagnostic assay is performed as follows. Target antigen specific antibodies are immobilized on latex beads that are incubated with bacteria present in or isolated from body fluids. Positive reaction can be detected by naked eye due to the aggregation of the coloured latex beads in the presence of the corresponding cognate antigen expressed on the surface of the bacteria.

A body fluid as used according to the present invention includes biological samples of a subject, such as tissue extract, urine, blood, serum, stool and phlegm.

In one embodiment the method comprises contacting a solid support with an excess of a certain type of antibody fragment which specifically forms a complex with the target, under conditions permitting the antibody to attach to the surface of the solid support. The resulting solid support to which the antibody is attached is then contacted with a biological fluid sample so that the target in the biological fluid binds to the antibody and forms a target-antibody complex. The complex can be labeled with a detectable marker. Alternatively, either the target or the antibody can be labeled before the formation the complex. For example, a detectable marker (label) can be conjugated to the antibody. The complex then can be detected and quantitatively determined thereby detecting and quantitatively determining the concentration of the target in the biological fluid sample.

For particular applications the antibody of the invention is conjugated to a label or reporter molecule, selected from the group consisting of organic molecules, enzyme labels, radioactive labels, colored labels, fluorescent labels, chromogenic labels, luminescent labels, haptens, digoxigenin, biotin, metal complexes, metals, colloidal gold and mixtures thereof. Antibodies conjugated to labels or reporter molecules may be used, for instance, in assay systems or diagnostic methods, e.g. to diagnose MDR *E. coli* infection or disease conditions associated therewith.

The antibody of the invention may be conjugated to other molecules which allow the simple detection of said conjugate in, for instance, binding assays (e.g. ELISA) and binding studies.

Another aspect of the present invention provides a kit comprising an antibody, which may include, in addition to one or more antibodies, various diagnostic or therapeutic agents. A kit may also include instructions for use in a diagnostic or therapeutic method. Such instructions can be, for example, provided on a device included in the kit, e.g. tools or a device to prepare a biological sample for diagnostic purposes, such as separating a cell and/or protein containing fraction before determining the MDR *E. coli* load to diagnose a disease. Advantageously, such a kit includes an antibody and a diagnostic agent or reagent that can be used in one or more of the various diagnostic methods described herein. In another preferred embodiment, the kit includes an antibody, e.g. in the lyophilized form, optionally including instructions and a medium to reconstitute the lyophilizate, and/or in combination with pharmaceutically acceptable carrier(s) that can be mixed before use to form an injectable composition for near term administration.

The antibodies designated 8D5-1G10 and 8D10-C8, specifically any of the antibody light chains and/or heavy chains, is further characterized by the biological material deposited at the DSMZ—Deutsche Sammlung von Mikroorganismen and Zellkulturen, Mascheroder Weg 1b/Inhoffenstraße 7B, 38124 Braunschweig (DE).

The deposits refer to transformed *E. coli* cultures, each containing a plasmid cloned with an insert of a gene of interest. The genes of interest are the variable domains of the heavy and light chains of the mouse monoclonal antibody 8D5-1G10 (IgG3), and the heavy and light chains of the mouse monoclonal antibody 8D10-C8 (IgG2b).

DSM 26763 is an *E. coli* host cell transformed with a plasmid comprising the variable domain coding sequence of the 8D5-1G10 light chain (8D5-1G10-LC). *Escherichia coli* 8D5-1G10-VL=DSM 26763, deposition date: Jan. 15, 2013; depositor: Arsanis Biosciences GmbH, Vienna, Austria.

DSM 26762 is an *E. coli* host cell transformed with a plasmid comprising the variable domain coding sequence of the 8D5-1G10 heavy chain (8D5-1G10-HC). *Escherichia coli* 8D5-1G10-VH=DSM 26762, deposition date: Jan. 15, 2013; depositor: Arsanis Biosciences GmbH, Vienna, Austria.

DSM 28171 is an *E. coli* host cell transformed with a plasmid comprising the variable domain coding sequence of the 8D10-C8 light chain (8D10-C8-LC). *Escherichia coli* 8D10-C8-VL=DSM 28171, deposition date: Dec. 11, 2013; depositor: Arsanis Biosciences GmbH, Vienna, Austria.

DSM 28172 is an *E. coli* host cell transformed with a plasmid comprising the variable domain coding sequence of the 8D10-C8 heavy chain (8D10-C8-HC). *Escherichia coli* 8D10-C8-VH=DSM 28172, deposition date: Dec. 11, 2013; depositor: Arsanis Biosciences GmbH, Vienna, Austria.

The subject matter of the following definitions is considered embodiments of the present invention:

1. An isolated antibody that specifically binds to O25b antigen of multi drug resistant (MDR) *E. coli* strains.

2. Antibody according to definition 1, which is cross-specific to bind the O25b and O25 antigens and/or preferentially binds to the O25b antigen relative to an O25a antigen of *E. coli*, preferably with a higher affinity as compared to binding the O25b antigen by a polyclonal serum raised against O25 (now known and herein referred to as O25a) *E. coli* strains as determined by immunoassay, compared to polyclonal typing serum raised against O25a strains, preferably wherein the antibody has at least equal affinity to both, the O25b and the O25a antigens, as determined by immunoassay, preferably immunoblotting, ELISA or other immunological methods.

3. Antibody according to definition 1 or 2, wherein the O25b antigen is prevalent in one or more ST131-O25b:H4 strains.

4. Antibody according to any of definitions 1 to 3, wherein the epitope recognized by the antibody is present on the surface of encapsulated and non-encapsulated ST131-O25b:H4 strains.

5. Antibody according to any of definitions 1 to 4, which has a binding site of a full-length monoclonal antibody or an antibody fragment thereof comprising at least one antibody domain incorporating a binding site, which antibody is preferably an antibody selected from the group consisting of murine, lama, rabbit, goat cow, chimeric, humanized or human antibodies, heavy-chain antibodies, Fab, Fd, scFv and single-domain antibodies like VH, VHH or VL, preferably a human IgG1 antibody.

6. Antibody according to any of definitions 1 to 5, which has an affinity to bind the O25b antigen with a Kd of less than $10^{-7}$ M, preferably less than $10^{-8}$ M.

7. Antibody according to any of definitions 1 to 6, which exhibits in vitro bactericidal potency in a serum sample comprising live wild-type MDR *E. coli* strains, and/or which stimulates uptake of live wild-type MDR *E. coli* strains by phagocytic cells in vitro.

8. Antibody according to any of definitions 1 to 7, wherein the antibody binds the same epitope as the antibody designated as 8D5-1G10 or 8D10-C8.

9. Antibody according to any of definitions 1 to 8, wherein the antibody comprises the same binding site as an antibody designated as 8D5-1G10 or 8D10-C8.

10. Antibody according to any of definitions 1 to 9, wherein the antibody is derived from an antibody, which is characterized by a variable region, which is
   obtainable from a host cell deposited under DSM 26763 and/or DSM 26762, or a functionally active variant thereof; or
   obtainable from a host cell deposited under DSM 28171 and/or DSM 28172, or a functionally active variant thereof.

11. Antibody according to definition 10, comprising
A
(a) a variable region of the antibody light chain produced by or obtainable from a host cell deposited under DSM 26763; and/or
(b) a variable region of the antibody heavy chain produced by or obtainable from a host cell deposited under DSM 26762;
(c) or a functionally active variant of (a) and/or (b)
or B
(a) a variable region of the antibody light chain produced by or obtainable from a host cell deposited under DSM 28171; and/or
(b) a variable region of the antibody heavy chain produced by or obtainable from a host cell deposited under DSM 28172;
(c) or a functionally active variant of (a) and/or (b).

12. Antibody according to definition 10 or 11, wherein the functionally active variant comprises a CDR with an amino acid sequence having at least 60% sequence identity.

13. Antibody according to any of definitions 10 to 12, wherein the functionally active variant differs from the parent antibody in at least one point mutation in the amino acid sequence, preferably in the CDR, wherein the number of point mutations in each of the CDR amino acid sequences is either 0, 1, 2 or 3.

14. A plasmid comprising a nucleotide sequence
A
   encoding a variable region of the antibody light chain designated 8D5-1G10-LC comprised in a host cell deposited under DSM 26763; and/or
   encoding a variable region of the antibody heavy chain designated 8D5-1G10-HC comprised in a host cell deposited under DSM 26762;
or B
   encoding a variable region of the antibody light chain designated 8D10-C8-LC comprised in a host cell deposited under DSM 28171; and/or
   encoding a variable region of the antibody heavy chain designated 8D10-C8-HC comprised in a host cell deposited under DSM 28172.

15. An expression cassette comprising a coding sequence to express a light chain and/or heavy chain of an antibody according to any of claims 1 to 13, which expression cassette or coding sequence is derived from a plasmid according to definition 14.

16. Method of producing an antibody according to any of definitions 1 to 13, wherein a host cell is transformed with a plasmid of claim 14 or the expression cassette according to definition 15.

17. A host cell comprising a plasmid according to definition 14 or the expression cassette according to definition 15.

18. The host cell according to definition 17, which is deposited under
   A
   DSM 26763 and/or DSM 26762;
   or B
   DSM 28171 and/or DSM 28172.

19. Method of producing an antibody according to any of definitions 1 to 13, wherein a host cell according to claim 17 or 18 is cultivated or maintained under conditions to produce said antibody.

20. A method of identifying a candidate antibody comprising:
   (a) providing a sample containing an antibody or antibody-producing cell; and
   (b) assessing for binding of an antibody in or produced by the sample with an epitope recognized by the antibody designated as 8D5-1G10 or 8D10-C8, wherein a positive reaction between the antibody and the epitope identifies the antibody as candidate antibody.

21. A method of identifying a candidate antibody comprising:
   (a) providing a sample containing an antibody or antibody-producing cell; and
   (b) assessing for binding of an antibody in or produced by the sample with O25b antigen of a ST131-O25b:H4 strain and O25a antigen of a non-MDR *E. coli* strain, wherein a specific positive reaction between the antibody and the O25b antigen relative to the O25a antigen identifies the antibody as candidate antibody.

22. A method of producing an antibody according to any of definitions 1 to 13, comprising
   (a) providing a candidate antibody identified according to claim 20 or 21; and
   (b) producing a monoclonal antibody, or a humanized or human form of the candidate antibody, or a derivative thereof with the same epitope binding specificity as the candidate antibody.

23. A method of producing an antibody according to any of definitions 1 to 13, comprising
   (a) immunizing a non-human animal with an epitope recognized by the antibody designated as 8D5-1G10 or 8D10-C8;
   (b) forming immortalized cell lines from the isolated B-cells;
   (c) screening the cell lines obtained in b) to identify a cell line producing a monoclonal antibody that binds to the epitope; and
   (d) producing the monoclonal antibody, or a humanized or human form of the antibody, or a derivative thereof with the same epitope binding specificity as the monoclonal antibody.

24. A method of producing an antibody according to any of definitions 1 to 13, comprising
   (a) immunizing a non-human animal with O25b antigen of a ST131-O25b:H4 strain and isolating B-cells producing antibodies;

(b) forming immortalized cell lines from the isolated B-cells;

(c) screening the cell lines to identify a cell line producing a monoclonal antibody that preferentially binds to the O25b antigen relative to the O25a antigen of *E. coli*; and (d) producing the monoclonal antibody, or a humanized or human form of the antibody, or a derivative thereof with the same epitope binding specificity as the monoclonal antibody.

25. Antibody according to any of definitions 1 to 13, for use in treating a subject at risk of or suffering from a MDR *E. coli* infection comprising administering to the subject an effective amount of the antibody to limit the infection in the subject or to ameliorate a disease condition resulting from said infection, preferably for treatment or prophylaxis of pyelonephritis, secondary bacteremia, sepsis, peritonitis, meningitis, and ventilator-associated pneumonia.

26. Antibody for use according to definition 25, for bactericidal killing of MDR *E. coli*, preferably a ST131-O25b:H4 strain irrespective of capsular polysaccharide expressed by the strain.

27. Antibody for use according to definition 25 or 26, wherein the antibody is administered in a parenteral or mucosal formulation.

28. Pharmaceutical preparation of an antibody according to any of definitions 1 to 13, preferably comprising a parenteral or mucosal formulation, optionally containing a pharmaceutically acceptable carrier or excipient.

29. Antibody according to any of definitions 1 to 13, for diagnostic use to determine *E. coli* infection in a subject caused by MDR strains expressing the LPS O25b, such as with upper and lower urinary tract infections, including cystitis or urethritis, ascending or hematogenous pyelonephritis, especially in diabetic patients, as well as with bacteremia, sepsis, peritonitis, or intestinal colonization.

30. Antibody for use according to definition 29, wherein a systemic infection with MDR *E. coli* in a subject is determined ex vivo by contacting a sample of body fluid of said subject with the antibody, wherein a specific immune reaction of the antibody determines the infection.

31. Antibody for use according to definition 29 or 30, wherein a sample of body fluid is tested for the specific immune reaction, which sample is selected from the group consisting of urine, blood, blood isolates or blood culture, aspirate, sputum, lavage fluid of intubated subjects and stool.

32. Antibody for use according to any of definitions 29 to 31, wherein the serotype of *E. coli* is determined in vitro from a pure *E. coli* culture recovered from a clinical specimen.

33. Diagnostic preparation of an antibody according to any of definitions 1 to 13, optionally containing the antibody with a label and/or a further diagnostic reagent with a label and/or a solid phase to immobilize at least one of the antibody and the diagnostic reagent.

34. Isolated epitope recognized by the antibody designated as 8D5-1G10 or 8D10-C8.

35. An immunogen comprising:
(a) an epitope according to definition 34;
(b) optionally further epitopes not natively associated with said epitope of (a); and
(c) a carrier.

36. Immunogen according to definition 35, wherein said carrier is a pharmaceutically acceptable carrier, preferably comprising buffer and/or adjuvant substances.

37. Immunogen according to definition 35 or 36, in a vaccine formulation, preferably for parenteral use.

38. Immunogen according to any of definitions 35 to 37, for use in treating a subject by administering an effective amount of said immunogen to protect the subject from an MDR *E. coli* infection, or to prevent a disease condition resulting from said infection.

39. Immunogen according to definition 38, for eliciting a protective immune response.

40. Isolated nucleic acid encoding an antibody according to any of definitions 1 to 13 or an epitope according to definition 35.

The foregoing description will be more fully understood with reference to the following examples. Such examples are, however, merely representative of methods of practicing one or more embodiments of the present invention and should not be read as limiting the scope of invention.

EXAMPLES

Example 1: O25b Specific Antibodies

We generated a non-encapsulated mutant of a representative ST131-O25b:H4 strain 81009 (81009Δkps::kan, [Szijarto et al, FEMS Microbiol Lett, 2012, 332:131-6]) by replacing the kps cluster (encoding capsular synthesis) with a cassette encoding kanamycin resistance. Sublethal doses of live or formaldehyde-inactivated cells of this mutant strain were used to immunize mice 4 times at two-week intervals. Subsequently, serum samples obtained from the mice were analysed, and the spleen of the mouse showing the highest IgG titer against O25b antigen (in ELISA, immunoblotting, and surface staining) was used for hybridoma generation. Following sub-cloning, several hybridoma clones were selected, which secreted antibodies specific to purified O25b antigens as well as bound to the surface of live wild-type *E. coli* strains expressing O25b antigens. These mAbs were purified from hybridoma supernatants for further testing.

As depicted on FIG. 1, all antibodies bound to several different clinical isolates determined to be ST131-O25b:H4 strains irrespective of the capsular polysaccharide expressed (K5, K2, or unknown K types). With respect to binding to strains expressing the O25a antigen there were two types of mAbs identified. One group represented by mAb 8D5-1G10, did not bind to the surface of O25a strains, while the other group of mAbs represented by 8D10-C8 was cross-reactive to O25a strains. None of the mAbs, however, could bind to any *E. coli* strains expressing unrelated antigens, i.e. O2. (FIG. 1) or other O-types (not shown).

The specificity of mAbs was further confirmed by immunoblot analysis using purified LPS (FIG. 2). The mAbs recognized the LPS molecules from ST131 strains containing the O25b antigen, however were different in their cross-reactive potential to O25a LPS antigens. While mAb 8D5-1G10 reacted exclusively to O25b antigen, mAb 8D10-C8 was cross-reactive to O25a. This observed cross-reactivity was compared to that exhibited by commercial O25 typing serum (Statens Serum Institut, high titer *E. coli* O25 antiserum, #81369) routinely used for the detection of ST131:O25b strains). The commercial rabbit serum showed clear preference towards binding to O25a antigens vs. O25b LPS. In contrast, murine mAb 8D10-C8 reacted to O25b LPS molecules at least with the same intensity as to the O25a molecules. Subsequent quantitative analysis revealed that the ratio of binding intensity to O25b vs O25a is at least 10-fold higher in case of mAb 8D10-C8 in comparison to the commercial typing serum.

The above data together suggest that there are two types of O25b-specific mAbs, those, which are highly specific to O25b, and those that recognize an epitope shared by O25a and O25b antigens. Consequently, our data confirms that the structure of O25b indeed differs from that of classical O25 (i.e. O25a) antigen. The novel structure of the O25b subunit was elucidated as described in Example 2.

The variable domains of the heavy (VH) and light (VL) chains of O25b-specific mAbs were amplified from hybridoma clones by using RT-PCR with degenerated heavy and light chain primers and sequenced. Sequences were analysed with BLAST for Ig database as well as with IMGT/V-QUEST, and CDR regions were defined according to Kabat nomenclature.

The variable light and heavy chain sequences of mAb 8D5-1G10 were cloned into respective vectors, which were used to transform the *E. coli* host cells deposited in DSMZ under accession numbers: DSM 26763 and DSM 26762.

The variable light and heavy chain sequences of mAb 8D10-C8 were cloned into respective vectors, which were used to transform the *E. coli* host cells deposited in DSMZ under accession numbers: DSM 28171 and DSM 28172.

Example 2: Structure Analysis of O25b Antigen

The LPS of *E. coli* ST131 was isolated by the hot phenol/water method and purified by dialysis, proteinase K digest and ultracentrifugation. The average yield of LPS preparations was 2.61% of dry bacterial mass. LPS was analysed by SDS-PAGE, showing fractions consisting of core oligosaccharide (OS) substituted with different numbers of oligosaccharide repeating units (RU) as well as unsubstituted core oligosaccharides. The O-specific polysaccharide (O-PS) and different oligosaccharide components were released by mild acidic hydrolysis and isolated by gel filtration on Bio-Gel P-10. The fractions were analysed by sugar and methylation analyses, NMR spectroscopy and MALDI-TOF mass spectrometry (MS).

The structure of the O-PS RU was determined with the use of a fraction consisted of the core OS substituted with one single RU. Monosaccharide analysis indicated the presence of Rha, Glc, Gal, Hep, and smaller amount of GlcN. Equimolar amounts of derivatives of terminal Rhap, terminal Glcp, 3,6-substituted Glcp, 3-substituted Rhap, with trace amounts 3-substituted GlcpN were identified and designated to the O-PS RU. Remaining partially methylated alditol acetates of 7-substituted Hepp, 6-substituted Glcp, 2-substituted Glcp, terminal Galp, 3,6-substituted Glcp, and terminal Hepp constituted the core oligosaccharide of K-12 type. Derivatives of 3,4-substituted Hepp, 3,4,7-substituted Hepp, and Kdo could not be detected during standard methylation and sugar analysis due to the substitution by P and PPEtn and presence of carboxyl group, respectively.

The structure of the RU of the O-specific PS of LPS ST131 was determined with the use of NMR spectroscopy. The complete assignment of the O-PS $^1$H and $^{13}$C resonances was achieved by combining the information obtained from COSY, TOCSY and NOESY, as well as HSQC-DEPT, HMBC, and HSQC-TOCSY experiments. The $^1$H, $^{13}$C HSQC-DEPT spectrum contained signals for 13 anomeric protons and carbons, and one Kdo spin system. These signals derived from the core oligosaccharide as well as from the one RU of the O-specific PS. The high-field region contained one signal of CH3 of O-acetyl group, one signal of CH3 of N-acetyl group, as well as two upfield signals of CH3 characteristic for the 6-deoxy sugars (Rha). The spectra indicated a tetradecasaccharide structure of the investigated oligosaccharide. Due to the high heterogeneity related to P, PP, and PEtn, the complete spin systems of eight sugars of the non-reducing end were completely resolved with emphasis on the RU structure and its linkage to the K-12 core OS.

The inter-residue connectivities between adjacent sugar residues were observed by NOESY and HMBC experiments. The HMBC spectra exhibited cross-peaks between the anomeric proton and the carbon at the linkage position and between the anomeric carbon and the proton at the linkage position, which confirmed the sequence of sugar residues in the non-reducing region of the polysaccharide.

Based on these measurements, the repeating unit of the O25b-specific PS was determined (FIG. 3 (*a*)), which is a pentasaccharide with →3)-β-GlcpNAc (residue K) as a residue of RU substituting the first residue of the core OS: →7)-α-Hepp (residue L). Due to a possible contamination of the longer PS fractions, it was impossible to identify position of substitution of the first RU by subsequent RU of the O-specific chain. Moreover without further detailed structural analyses of those fractions, the presence of GlcNAc in subsequent repeating units as α-anomer (what was previously reported for some of *E. coli* lipopolysachcrides) could be ruled out.

Molecular weights of the core OS, core OS substituted with one RU, and finally the O-PS RU was confirmed with the use of MALDI-TOF MS (data not shown). All spectra were interpreted on the basis of elucidated herein structure of the RU of LPS ST131 and previously identified glycoforms of K-12 core OS (Duda et al. Microbiology. 2011 June; 157(Pt 6):1750-60. doi: 10.1099/mic.0.046912-0. Epub 2011 Mar. 3; Muller-Loennies et al. J Biol Chem. 2003 Sep. 5; 278(36):34090-101. Epub 2003 Jun. 20). MALDI-MS analysis of low resolution spectra of fraction consisting of core OS substituted with shorter O-PS showed clusters of ions with following prevailing ions: m/z 2797.2, m/z 3659.6, m/z 4522.0, and m/z 5383.6 attributed to core OS (with P and PPEtn) substituted with 1, 2, 3, and 4 RUs, respectively. Average mass difference among these ions was 862.1 Da and matched calculated average mass of the O-specific PS RU (861.8 Da, RU-H2O).

Taking into consideration the molecular weight of the RU and comparing MS results for other fractions, we have shown the presence of longer core OS glycoform consisting →7)-α-Hepp-(1→6)-α-Glcp disaccharide in the outer core region as a place of substitution with the first RU (FIG. 3 (*a*)). It was shown that LPS ST131 consisted of two main core OS glycoforms. The type of glycoform is dependent on the presence or absence of the O-specific PS. Prevailing glycoform of the unsubstituted core OS is truncated version of K-12 core oligosaccharide, which is devoid of →7)-α-Hepp-(1→6)-α-Glcp disaccharide. Such disaccharide is the difference between O-PS substituted core OS and nonsubstituted core OS.

Example 3: *E. coli* O25b Specific Diagnostic Assay

The O25b-specific mAb 8D5-1G10 was bound to 1 μm diameter latex beads (Polysciences) by following instructions of the manufacturer. Latex-coupled beads were tested for their potential to agglutinate different *E. coli* strains. A loopful of bacteria (approx. $10^8$ cfu) was mixed with 10 μl of 1% suspension of mAb-coupled latex beads in PBS. As depicted on FIG. 4 *E. coli* strains expressing O25b antigens showed a strong agglutination pattern after gentle agitation for a few seconds. On the contrary, *E. coli* strains expressing O25a or O2 antigens did not agglutinate with the same reagent. Therefore, this putative diagnostic reagent is considered to be more specific than the currently used state of the art agglutination reagent (i.e. polyclonal rabbit serum against O25) used for the detection of O25b (and O25a)-positive E. coli.

Furthermore, as commercial anti-O25 serum is recommended to be used with heat killed (i.e. lysed) E. coli cells in agglutination assays, we tested, whether O25b mAbs—either purified or coupled to latex beads—would have a higher sensitivity, i.e. whether they are able to agglutinate live E. coli cells in the presence of intact capsular polysaccharides. A large panel of O25b clinical isolates were tested and results with some representative strains are presented in Table I. Improvement in sensitivity was found in two respects: i) representative strains #1 and #2 were agglutinable with both free or bead-coupled O25b-specific mAbs in a non-heat killed (i.e. live bacteria directly taken from an agar plate) form, while agglutination with the commercial O25 rabbit serum required prior heat-lysis of the bacteria, ii) representative strains #3 and #4 were not able to be agglutinated with the commercial serum even in a heat killed form, whereas the same lysates gave positive result with the purified mAb 8D5-1G10. Importantly, when the same antibody was coupled to latex beads, agglutination developed even with native bacterial cells. These results indicate a superior sensitivity of the bead-coupled mAbs in an agglutination assays, which is corroborated by the fact that all O25b positive E. coli strains tested so far gave a positive agglutination with this reagent even without any prior treatment (i.e. without producing a heat-killed lysate). Moreover, using this reagent as a diagnostic tool for the detection of O25b-expressing bacteria has the advantage over PCR based technique that it only gives a positive result with bacteria in fact expressing the target antigen. For instance, representative strain #5 in Table I was PCR positive for the O25b specific gene routinely used in diagnostics, however, was negative in any agglutination assays. This strain has been proven to exhibit a rough LPS phenotype (no O-antigens expressed), therefore, the PCR result could be considered as false positive. Avoiding such false positivity is of great importance, when such assays are used as companion diagnostics, i.e. to select patients infected with O25b expressing E. coli strain that could benefit from O25b specific therapeutic approaches.

The potential of detecting free O25b LPS molecules by the latex bead-coupled mAbs was also tested. Different amounts of highly purified O25b LPS in the range of 1-1000 ng were incubated with 10 µl of 1% bead suspension in PBS. As depicted on FIG. 5, a dose dependent agglutination pattern was seen: the best results were obtained with 100 ng of free LPS, agglutination was still detectable with 1000 or 10 ng, while was undetectable with 1 ng of free O25b LPS.

TABLE I

Comparison of agglutination results obtained with various O25b strains using commercial O25 typing serum and O25b specific mAb 8D5-1G10.

| O25b strain | rfb$_{O25b}$ PCR | Agglutination by O25 typing serum (commercial) of heat-killed lysates | Agglutination by O25b mAbs of Lysates (heat-killed) | Live cells (non heat-killed) | Agglutination by 8D5-1G10 coupled beads of live (non heat-killed) bacteria |
|---|---|---|---|---|---|
| #1 | + | + | + | + | + |
| #2 | + | + | + | + | + |
| #3 | + | − | − | + | + |
| #4 | + | − | − | + | + |
| #5 | + | − | − | − | − |

Example 4: Antibacterial Effect of O25b Specific mAbs

The potential protective effect of O25b-specific mAbs (with or without cross-reactivity to O25a) was tested in a lethal murine bacteremia model. Groups of 5 mice received 100 µg of purified 8D5-1G10 or 8D10-C8, intraperitoneally. 24 h later mice were challenged intravenously by a lethal dose (previously determined in a pilot experiment) of E. coli strain 81009 ($2 \times 10^8$ CFU/mouse) expressing the O25b antigen. Lethality of mice was monitored daily for 3 weeks. FIG. 6 shows combined results of 2 independent experiments with similar outcome. While 90% of the mice mock immunized with PBS succumbed to infection, both mAbs tested provided statistically (Logrank test) significant increase in survival over the 3-week post-infection period monitored.

In order to corroborate this in vivo data, bactericidal effect of purified mAbs was also tested in vitro. 2 ml of a mid-log culture of E. coli strain 81009 was washed twice in PBS and re-suspended to a final concentration of $5 \times 10^5$ CFU/ml. 10 µl of this bacterial suspension was pre-incubated for 15 minutes at 4° C. with 4 µg of the respective mAbs diluted in 40 µl RPMI-1640 buffer supplemented with 3% human albumin. Subsequently, 50 µl of pooled human serum (previously adsorbed with E. coli strain 81009) was added to the reaction and incubated at 37° for 1, 2 and 3 hrs. The final CFU and antibody concentrations in the reaction were $5 \times 10^4$ CFU/ml and 40 µg/ml respectively in a total volume of 100 µl. 10 µl aliquots were plated onto TSB plates for colony counting at the specified time points.

As depicted on FIG. 7, both mAbs tested were able to significantly decrease the CFU over the 3 hours study period. In contrast, the bacteria mixed with an irrelevant mAb or no antibodies showed constant growth in this medium. In case complement was inactivated in the serum samples (by 30 min. incubation at 56° C.), no bacterial killing was observed by any mAbs (data not shown). These results prove that both O25b-specific mAbs can trigger complement mediated bactericidal effect.

The invention claimed is:
1. A monoclonal antibody composition comprising:
   an isolated monoclonal antibody that specifically binds to 025b antigen of multi drug resistant (MDR) E. coli strains, and
   a carrier or excipient.
2. A monoclonal antibody composition comprising:
   a) an isolated monoclonal antibody that specifically binds to 025b antigen of multi drug resistant (MDR) E. coli strains which comprises:

the variable region of the antibody light chain produced by the host cell deposited under DSM 26763; and the variable region of the antibody heavy chain produced by the host cell deposited under DSM 26762; and b) a carrier or excipient.

3. A monoclonal antibody composition comprising:

a) an isolated monoclonal antibody that specifically binds to 025b antigen of multi drug resistant (MDR) *E. coli* strains which comprises:

the variable region of the antibody light chain produced by the host cell deposited under DSM 28171; and the variable region of the antibody heavy chain produced by the host cell deposited under DSM 28172; and b) a carrier or excipient.

4. A pharmaceutical preparation of an antibody of claim 1, comprising a parenteral or mucosal formulation, containing a pharmaceutically acceptable carrier or excipient.

5. A diagnostic preparation of an antibody of claim 1 containing the antibody with a label and/or a further diagnostic reagent with a label and/or a solid phase to immobilize at least one of the antibody and the diagnostic reagent.

* * * * *